United States Patent
Qi et al.

(10) Patent No.: US 9,417,243 B2
(45) Date of Patent: *Aug. 16, 2016

(54) SYSTEMS AND METHODS FOR ANTI-PAX8 ANTIBODIES

(71) Applicant: Biocare Medical, LLC, Concord, CA (US)

(72) Inventors: Weimin Qi, Martinez, CA (US); David Tacha, Vacaville, CA (US)

(73) Assignee: Biocare Medical, LLC, Concord, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/507,667

(22) Filed: Oct. 6, 2014

(65) Prior Publication Data

US 2015/0056635 A1 Feb. 26, 2015

Related U.S. Application Data

(63) Continuation of application No. 14/004,400, filed as application No. PCT/US2012/037367 on May 10, 2012, now Pat. No. 8,852,592.

(60) Provisional application No. 61/484,579, filed on May 10, 2011, provisional application No. 61/588,035, filed on Jan. 18, 2012.

(51) Int. Cl.
*A61K 39/395* (2006.01)
*G01N 33/574* (2006.01)
*C07K 16/18* (2006.01)
*C07K 16/32* (2006.01)

(52) U.S. Cl.
CPC ............ *G01N 33/5748* (2013.01); *C07K 16/18* (2013.01); *C07K 16/32* (2013.01); *G01N 33/574* (2013.01); *C07K 2317/24* (2013.01); *C07K 2317/34* (2013.01); *C07K 2317/56* (2013.01)

(58) Field of Classification Search
None
See application file for complete search history.

(56) References Cited

U.S. PATENT DOCUMENTS

| | | | |
|---|---|---|---|
| 4,145,406 A | 3/1979 | Schick et al. | |
| 4,254,082 A | 3/1981 | Schick et al. | |
| 4,687,732 A | 8/1987 | Ward et al. | |
| 4,690,890 A | 9/1987 | Loor et al. | |
| 4,792,521 A | 12/1988 | Shochat | |
| 4,863,875 A | 9/1989 | Bailey et al. | |
| 5,089,423 A | 2/1992 | Diamandis et al. | |
| 5,108,896 A | 4/1992 | Philo et al. | |
| 5,252,487 A | 10/1993 | Bacus et al. | |
| 5,482,698 A | 1/1996 | Griffiths | |
| 5,487,975 A | 1/1996 | Miller et al. | |
| 5,565,332 A | 10/1996 | Hoogenboom et al. | |
| 5,620,845 A | 4/1997 | Gould et al. | |
| 5,691,154 A | 11/1997 | Callstrom et al. | |
| 5,719,063 A | 2/1998 | Block | |
| 5,869,274 A | 2/1999 | Tsao et al. | |
| 5,891,658 A | 4/1999 | Klainer et al. | |
| 6,008,057 A | 12/1999 | Glass et al. | |
| 6,051,693 A | 4/2000 | Handley et al. | |
| 6,252,053 B1 | 6/2001 | Ohbayashi et al. | |
| 6,403,769 B1 | 6/2002 | Larochelle et al. | |
| 6,409,990 B1 | 6/2002 | Vera | |
| 6,476,206 B1 | 11/2002 | Sidransky et al. | |
| 6,537,745 B2 | 3/2003 | Chien et al. | |
| 6,580,056 B1 | 6/2003 | Tacha | |
| 6,723,506 B2 | 4/2004 | Fletcher et al. | |
| 6,946,256 B1 | 9/2005 | McKeon et al. | |
| 7,422,739 B2 | 9/2008 | Anderson et al. | |
| 7,468,425 B2 | 12/2008 | Sidransky et al. | |
| 7,674,605 B2 | 3/2010 | Lin et al. | |
| 7,785,803 B2 | 8/2010 | Achen et al. | |
| 7,846,726 B2 | 12/2010 | Li et al. | |
| 7,846,762 B2 | 12/2010 | Rana et al. | |
| 7,875,705 B2 | 1/2011 | Iwanari et al. | |
| 7,935,794 B2 | 5/2011 | Pullen | |
| 7,935,795 B2 | 5/2011 | Nakajima | |
| 7,935,796 B2 | 5/2011 | Lee et al. | |
| 7,973,138 B2 | 7/2011 | Liang et al. | |
| 8,153,126 B2 | 4/2012 | Violette et al. | |
| 8,168,409 B2 | 5/2012 | Calzone et al. | |
| 8,338,576 B2 | 12/2012 | Paralkar et al. | |
| 8,603,765 B2 | 12/2013 | Tacha | |
| 8,852,592 B2 * | 10/2014 | Qi et al. ................. 424/138.1 |
| 9,005,612 B2 | 4/2015 | Ledbetter et al. | |
| 9,156,915 B2 | 10/2015 | Waldman et al. | |
| 2002/0106685 A1 | 8/2002 | Henning et al. | |
| 2002/0173053 A1 | 11/2002 | Damaj et al. | |
| 2003/0017491 A1 | 1/2003 | Shi et al. | |
| 2005/0186642 A1 | 8/2005 | Tacha | |

(Continued)

FOREIGN PATENT DOCUMENTS

EP 2402370 A1 1/2012
EP 1733437 B1 9/2014

(Continued)

OTHER PUBLICATIONS

Tacha et al. 'A 6-Anitbody Panel for the Classification of Lung Adenocarcinoma Versus Squamous Cell Carcinoma.' Appl Immunohistochem Mol Morphol. 20(3): 201-7, May 2012.
Baty et al. 'Gene profiling of Icinical routine biopsies and prefiction of survival in non-small cell lung cancer.' Am J Respir Crit Care Med. 181(2):181-8. Oct. 15, 2009.
Brown, et al. 'Tissue Preserving Antibody Cocktails to Differentiate Primary Squamous Cell Carcinoma, Adenocarcinoma, and Small Cell Carcinoma of Lung.' Arch Pathol Lab Med. 137(9):1274-81. Jan. 4, 2013.

(Continued)

*Primary Examiner* — Sheela J Huff
(74) *Attorney, Agent, or Firm* — Santangelo Law Offices, P.C.

(57) ABSTRACT

The present invention is related to the anti-PAX8 antibodies, kits, cocktails, and use of anti-PAX8 antibodies for detection of cancer.

23 Claims, 13 Drawing Sheets

(56) References Cited

U.S. PATENT DOCUMENTS

| | | |
|---|---|---|
| 2006/0148063 A1 | 7/2006 | Fauzzi et al. |
| 2007/0015908 A1 | 1/2007 | Fischer et al. |
| 2007/0041972 A1 | 2/2007 | Rother et al. |
| 2009/0191190 A1 | 7/2009 | Barghorn et al. |
| 2010/0047825 A1 | 2/2010 | Tacha |
| 2010/0092457 A1 | 4/2010 | Aburatani et al. |
| 2012/0082999 A1 | 4/2012 | Liao et al. |
| 2012/0245051 A1 | 9/2012 | Rimm et al. |
| 2012/0321557 A1 | 12/2012 | Kimura |
| 2014/0004542 A1 | 1/2014 | Qi et al. |
| 2015/0152180 A1 | 6/2015 | Davis et al. |
| 2016/0009795 A1 | 1/2016 | Tacha et al. |

FOREIGN PATENT DOCUMENTS

| | | |
|---|---|---|
| WO | 03003906 A2 | 1/2003 |
| WO | 2005054860 A1 | 6/2005 |
| WO | 2005076005 A2 | 8/2005 |
| WO | 2005083802 A1 | 9/2005 |
| WO | WO 2005/083802 A1 | 9/2005 |
| WO | 2010022736 A2 | 3/2010 |
| WO | 2010124689 A1 | 11/2011 |
| WO | 2012031273 A2 | 3/2012 |
| WO | 2012154983 A2 | 11/2012 |
| WO | 2012154983 A3 | 11/2012 |
| WO | 20120154983 A1 | 11/2012 |
| WO | WO 2012/154983 A2 | 11/2012 |
| WO | WO 2014/057803 A1 | 2/2014 |
| WO | 2014100220 A2 | 6/2014 |
| WO | 2014134587 A1 | 9/2014 |
| WO | 2014052672 A1 | 4/2015 |
| WO | 2015051320 A2 | 4/2015 |

OTHER PUBLICATIONS

Whithaus K., et al. Evaluation of Napsin A, Cytokeratin 5/6, p63, and Thyroid Transcription Factor 1 in Adenocarcioma Versus Squamous Cell Carcinoma of Lung. Arch Pathol Lab Med. 2012; 136: 155-162.

Savci-Heijink C. D., et al. The role of desmoglein-3 in the diagnosis of squamous cell carcinoma of the lung. Am J Pathol. 2009;174(5): 1629-1637.

Ring B. Z., et al. A novel five-antibody immunohisto- chemical test for subclassification of lung carcinoma. Mod Pathol. 2009;22(8): 1032-1043.

Mukhopadhyay S., et al. Subclassification of Non-small Cell Lung Carcinomas lacking Morphologic Differentiation on biopsy specimens: Utility of an Immunohistochemical Panel Containing TTF-1, Napsin A, p63 and CK 5/6. Am J Surg Pathol, 2011; 35(1): 15-25.

Bishop J. A., p40 (ΔNp63) is superior to p63 for the diagnosis of pulmonary squamous cell carcinoma, Modern Pathology (2011), 1-11; republished Mar. 2012;25(3):405-15.

Ikeda S, et al. "Combined immunohistochemistry of beta-catenin, cytokeratin 7, and cytokeratin 20 is useful in discriminating primary lung adenocarcinomas from metastatic colorectal cancer.", BMC Cancer. Feb. 2, 2006;6:31.

Chopra, N. et al. 'Inducing Protectice Antibodies Against Ring-Infected Erythrocyte Surface Peptide Antigen of Plasmodium Falciparum Using Immunostimulating Complex (Iscoms) Delivery.' Med Microbiol. Immunol. Nov. 2000 vol. 189, No. 2: pp. 75-83.

Calbiochem-Novabiochem International. P40(Ab-1) Cat# PC373 [datasheet]. USA 2000; 2 pages.

Abcam. Understanding Secondary Antibodies: Fragment Antigen Binding Antibodies and Isotopes. USA 2012; 12 pages.

Biocare Medical. MACH 2 Double-Stain 2 [datasheet]. USA Mar. 2, 2011; 2 pages.

Yamaguchi, K. et al. Circulating Antibodies to P40AIS in the Sera of Respiratory Tract Cancer Patients. Int. J. Cancer. Nov. 20, 2000. vol. 89 No. 6; 5 pages.

Vaidyanathan, P. Aperio-Definins Digital Pathology Solutions [Presentation]. Jul. 7, 2011. Aperio Webinar. <http://www.aperio.com/sites/default/files/events/070611_Spectrum_Plus_ppt_for_webinar_on_integration.pd>; 10 pages.

Jain, et al. Atypical ductal hyperplasia: interobserver and intraobserver variability. Mod. Pathol. (2011) 24, 917-923.

Tacha, et al. "An Immunohitochemical Analysis of a Newly Developed Mouse Monoclncal p40 (BC28) in Lung, Bladder, Skin, Breast, Prostate, and Head and Neck Cancers" 2014 College of American Pathologists, Early Online Release, Arch Pathol. Lab Med. 8 pages, postes Feb. 2014.

Barbareschi, et al. p63, a p53 homologue, is a selective nuclear marker of myoepithelial cells of the human breast. Am J Surg. Pathol 25(8): 1054-1060,Aug. 2001.

Bergholz, et al. 'Role of p63 in development, tumorigenesis and cancer progression'. Cancer Microenvironment (2012) 5:311-322.

Di Como, et al. 'p63 Expression Profiles in Human Normal and Tumor Tissues'. Clinical Cancer Research. vol. 8, 494-501, Feb. 2002.

Hibi, et al. 'AIS is an oncogene amplified in squamous cell carcinoma'. Pro Natl Acad Sci U.S.A, May 9, 2000, vol. 97, No. 10, 5462-5467.

Kaghdad, et al. Monoallelically Expressed Gene Related to p53 a 1p36, a Region Frequently Deleted in Neuroblastoma and Other Human Cancers. Cell, vol. 90(4), 809-819, Aug. 22, 1997.

Kami-Schmidt, et al. Distinct Expression Profiles of p63 Variants during Urothelial Development and Bladder Cancer Progression. Am J Pathol vol. 178, No. 3, Mar. 2011, 1350-60.

Khoury, et al. "p53 Isoforms: An Intracellular Microprocessor?" Genes & Cancer, 2(4), 2011, 453-465.

Murray-Zmijewski, et al. p53/p63/p73 isoforms: an orchestra of isoforms to harmonise cell differentiation and response to stress. Cell Death and Differentiation (Jun. 2006); 13(6), 962-972.

Nobre, et al. 'p40: A p63 isoform useful for lung cancer diagnosis—a Review of the Physiological and Pathological Role pf p63'. Acta Cytologica 2012; 57(1):1-8.

Nonaka, 'A study of Np63 expression in lung non-small cell carcinomas'. Am J Surg Pathol vol. 36 No. 6 Jun. 2012 895-9.

Nylander, et al. 'Differential expression of p63 isoforms in normal tissues and neoplastic cells'. J Pathol 2002; 198: 417-427.

Osada, et al. Cloning and functional analysis of human p51, which structurally and functinoally resembles p53, Nat Med. Jul. 1998; 4(7): 839-43.

Pelosi, et al. 'Np63 (p40) and Thyroid Transcription Factor-1 Immunoreactivity on small biopsies or cellblocks for typing non-small cell lung cancer'. Journal and Thoracic Oncology, vol. 7(2), No. 2, Feb. 2012, 281-90.

Senoo et al. 'A second p53-Related Protein, p73L, with High Homology to p73'. Biophys Res Commun. Jul. 30, 1998; 248(3), 603-607.

Trink, et al. A new human p53 homologue, Nat Med. Jul. 1998; 4(7): 747-8.

Yang, et al. 'p63, a p53 homolog at 3q27-29, encodes multiple products with transactivating, death-inducing, and dominant-negative activities'. Molecular Cell, vol. 2(3), 305-316, Sep. 1998.

Bowen, et al. 'Emerging roles for PAX8 in ovarian cancer and endosalpingeal development.' Gynecologic Oncology, vol. 104, No. 2, Feb. 2007, 331-337.

U.S. Appl. No. 61/706,312, filed Sep. 27, 2012; entitled Systems and Methods for Anti-Uroplakin II Antibodies.

U.S. Appl. No. 13/830,473, filed Mar. 14, 2013; entitled Systems and Methods for Anti-Uroplakin III Antibodies.

Brown, H. M. et al. Uroplakin-III to Distinguish Primary Vulvar Paget Disease From Paget Disease Secondary to Urothelial Carcinoma, Human Path. 2002;33:545-548.

Koga, F. et al. Impaired p63 Expression Associates with Poor Prognosis and Uroplakin III Expression in Invasive Urothelial Carcinoma of the Bladder, Clin Cancer Res. 2003;9:5501-5507.

Logani, S. et al. Immunoprofile of Ovarian Tumors With Putative Transitional Cell (Urothelial) Differentiation Using Novel Urothelial MarkersHistogenetic and Diagnostic Implications, Am J Surg Pathol 2003;27:1434-1441.

Matsumoto, K et al. Loss Expression of Uroplakin III is Associated with Clinicopathologic Features of Aggressive Bladder Cancer, Urology. 2008;72:444-449.

(56) References Cited

OTHER PUBLICATIONS

Mhawech, P. et al. Immunohistochemical Profile of High-Grade Urothelial Bladder Carcinoma and Prostate Adenocarcinoma, Human Path. 2002;33:1136-1140.

Ogawa, K. et al. Immunohistochemical Analysis of Uroplakins, Urothelial Specific Proteins, in Ovarian Brenner Tumors, Normal Tissues, and Benign and Neoplastic Lesions of the Female Genital Tract. Am J Pathol. 1999;155:1047-1050.

Ohtsuka, Y. et al. Loss of uroplakin III expression is associated with a poor prognosis in patients with urothelial carcinoma of the upper urinary tract, BJU International, 2006;97:1322-1326.

Parker, D. C. et al. Potential Utility of Uroplakin III, Thrombomodulin, High Molecular Weight Cytokeratin, and Cytokeratin 20 in Noninvasive, Invasive, and Metastatic Urothelial (Transitional Cell) Carcinomas, Am J Surg Pathol 2003;27:1-10.

Wu, X. R. et al. Mammalian Uroplakins, A group of highly conserved urothelial differentiation-related membrane proteins, J Biol Chem. 1994;269:13716-13724.

Moll, R. et al. Uroplakins, Specific Membrane Proteins of Urothelial Umbrella Cells, as Histological Markers of Metastatic Transitional Call Carcinomas. Am J Pathol, vol. 147, No. 5, Nov. 1995.

Kaufmann, O. et al. Uroplakin III Is a Highly Specific and Moderately Sensitive Immunohistochemical Marker for Primary and Metastatic Urothelial Carcinomas, Am J Clin Pathol 2000;113:683-687.

Wu, RL et al. Uroplakin II Gene is expressed in transitional cell carcinoma but not in bilharzial bladder squamous cell carcinoma: alternative pathways of bladder epithelial differentiation and tumor formation. Cancer Research, Mar. 15, 1998, vol. 58, No. 6, pp. 1291-1297.

Yu, C et al. PSA and NIKX3.1: A Comparative IHC Study of Sensitive and Specificity in Prostate Cancer. BioCareMedical, Presented at USCAP, Abstract #1070, Mar. 19-21, 2012. <uri: http://biocare.net/wp-content/uploads/PSANKX100.pdf>.

Wu XR, Kong XP, Pellicer A, Kreibich G, Sun TT.; Uroplakins in urothelial biology, function, and disease; Kidney Int. Jun. 2009;75(11):1153-65.

Wu X, Kakehi Y, Zeng Y, Taoka R, Tsunemori H, Inui M. J; Uroplakin II as a promising marker for molecular diagnosis of nodal metastases from bladder cancer: comparison with cytokeratin 20.; Urol. Dec. 2005;174(6):2138-4.

Olsburgh J, Harnden P, Weeks R, Smith B, Joyce A, Hall G, Poulsom R, Selby P, Southgate J.J; Uroplakin gene expression in normal human tissues and locally advanced bladder cancer Pathol. Jan. 2003;199(1):41-9.

Lu JJ, Kakehi Y, Takahashi T, Wu XX, Yuasa T, Yoshiki T, Okada Y, Terachi T, Ogawa O; Detection of circulating cancer cells by reverse transcription-polymerase chain reaction for uroplakin II in peripheral blood of patients with urothelial cancer; Clin Cancer Res. Aug. 2000;6(8):3166-71.

Li, S.M., et al. Detection of circulating uroplakin-positive cells in patients with transitional cell carcinoma of the bladder; J Urol. Sep. 1999;162(3 Pt 1):931-5.

Kong XT, Deng FM, Hu P, Liang FX, Zhou G, Auerbach AB, Genieser N, Nelson PK, Robbins ES, Shapiro E, Kachar B, Sun TT.; Roles of uroplakins in plaque formation, umbrella cell enlargement, and urinary tract diseases. J Cell Biol. Dec. 20, 2004;167(6)1195-204.

Okegawa T, Kinjo M, Nutahara K, Higashihara E.; Value of reverse transcription polymerase chain assay in peripheral blood of patients with urothelial cancer. J Urol. Apr. 2004;171(4):1461-6.

Hong-Ying Huang, Shahrokh F. Shariat, *Tung-Tien Sun, Herbert Lepor, Ellen Shapiro, Jer-Tsong Hsieh, Raheela Ashfaq, Yair Lotan, and Xue-Ru Wu, ; Persistent Uroplakin Expression in Advanced Urothelial Carcinomas: Implications in Urothelial Tumor Progression and Clinical Outcome. Hum Pathol. Nov. 2007; 38(11): 1703-1713.

Lai. Y. et al. UPK3A: A promising novel urinary marker for the detection of bladder cancer, Urology 76(2), 2010.

U.S. Appl. No. 61/727,559, filed Nov. 16, 2012; entitled Systems and Methods for Anti-Uroplakin III Antibodies.

Saeb, Parsy, et al. 'Diagnosis of Bladder Cancer by Immunocytochemical detection of minichromosome maintenance protein-2 in cells retrieved from urine' British Journal of Cancer (2012) 107, 1384-1391.

U.S. Appl. No. 61/941,907, filed Feb. 19, 2014; entitled Systems and Methods for Anti-SOX10 Antibodies.

International Application No. PCT/US13/62043, entitled Anti-Uroplakin II Antibodies Systems and Methods, filed Sep. 26, 2013, Search Report, dated Jan. 29, 2014. 6 pages.

International Application No. PCT/US13/62043, entitled Anti-Uroplakin II Antibodies Systems and Methods, filed Sep. 26, 2013, Written Opinion, dated Jan. 29, 2014. 22 pages.

Panka et al. Variable region framework differences result in decreased or increased affinity of variant anti-digoxin antibodies. Proc. Natl. Acad. Sci. USA, vol. 85, pp. 3080-3084, May 1988.

Harris et al. Assessing Genetic Heterogeneity in Production Cell Lines: Detection by Peptide Mapping of a Low Tyr to Gln Sequence Variant in a Recombinant Antibody. Biotechnology, vol. 11 p. 1293-1297, Nov. 1993.

Okazaki et al. Hydronephrosis associated with antiurothelial and antinuclear autoantibodies in BALB/ c-Fcgr2b-/-Pdcd1-/- mice. The Journal of Experimental Medicine. vol. 202, No. 12, pp. 1643-1648, Dec. 19, 2005.

International Application No. PCT/US14/59162, entitled Anti-SOX10 Antibody Systems and Methods, filed Oct. 3, 2014, Search Report, dated Apr. 13, 2015. 4 pages [SOX10PCT].

International Application No. PCT/USI4/59162, entitled Anti-SOX10 Antibody Systems and Methods, filed Oct. 3, 2014, Written Opinion dated Apr. 13, 2015. 8 pages [SOX10PCT].

Bondurand, et al. The role of SOX10 during enteric nervous system development. Dev Bioi. Epub May 2, 2013, 382(1):330-43.

GenBank Accession No. CAG30470. SOX10 (*Homo sapiens*]. Oct. 16, 2008. (Retrieved from the Internet Dec. 4, 2014: <http://www.ncbi.nlm.nih.gov/protein/CAG30470.1>] 2 pages.

International Application No. PCT/US13/76203, entitled Antibody Cocktail Systems and Methods for Classification of Histological Subtypes in Lung Cancer, filed Dec. 18, 2013, Search Report, dated Jul. 8, 2014. 6 pages.

International Application No. PCT/USI3/76203, entitled Antibody Cocktail Systems and Methods for Classification of Histological Subtypes in Lung Cancer, filed Dec. 18, 2013, Written Opinion, dated Jul. 8, 2014. 10 pages.

U.S. Appl. No. 61/738,938 entitled "Systems and Methods for Antibody Cocktails for Classification of Histologic Subtypes in Lung Cancer" filed Dec. 18, 2012.

International Application No. PCT/US14/19705, entitled Anti-p40 Antibodies Systems and Methods, filed Feb. 28, 2014, Search Report, dated May 23, 2014. 7 pages.

International Application No. PCT/US14/19705, entitled Anti-p40 Antibodies Systems and Methods, filed Feb. 28, 2014, Written Opinion, dated May 23, 2014. 27 pages.

Sanderson, SO et al., "An Analysis of the p63/α-Methylacyl Coenzyme A Racemase Immunohistochemical Cocktail Stain in Prostrate Needs Biopsy Speciments and Tissue Microarrays", Am. J. Clin. Path., 2004; 121:220-225.

Zhou, Ming. al., "Basal Cell Cocktail (34βE12 + p63) Improves the Detection of Prostate Basal Cells", Am. J. Surg. Path., 2003: 27(3), 365-371.

Zhou, Ming et al., "Expression and Disgnostic Utility of Alpha-Methylacyl-CoA-Racemase (P504S) in Foamy Gland and Pseudohyperplastic Prostate Cancer", Am. J. Surgical Pathology 27(6): 772-778, 2003.

Anonymous: "PIN cocktail-2 (P504S+p63)", Biocarta. May 4, 2003, pp. 1-2. XP 002667408, Retrieved from the Internet: URL:http://www.biocarta.com/TDS/PM205DSH.pdf [retrieved on Jan. 18, 2012].

Anonymous: "Double vision. The double stain, polymer detection system", Biocare Medical, Aug. 2, 2003, pp. 1-3, XP002667409, retrieved from the Internet: URL: htt12 ://web/archive. org/web/20030802112943/httQ :1/biocare. net/Detection. htm [retrieved Jan. 18, 2012].

Albadine, R. et al PAX8 (+)/p63 (−) immunostaining pattern in renal collecting duct carcinoma (CDC): a useful immunoprofile in the

(56) References Cited

OTHER PUBLICATIONS differential diagnosis of CDC versus urothelial carcinoma of upper urinary tract. Am J Surg Pathol 2010; 34:965-969.
Avery, A. K. et al. Use of antibodies to RCC and CD10 in the differential diagnosis of renal neoplasms. Am J Surg Pathol. Feb. 2000; 24(2):203-10.
Bowen N. J. et al. Emerging roles for PAX8 in ovarian cancer and endosalpingeal development. Gynecol Oncol. Feb. 2007; 104(2):331-7.
Haynes C. M. et al. PAX8 is expressed in pancreatic well-differentiated neuroendocrine tumors and in extrapancreatic poorly differentiated neuroendocrine carcinomas in fine-needle aspiration biopsy specimens. Cancer Cytopathol 2011; 119:193-201.
Kobel M. et al. Ovarian carcinoma subtypes are different diseases: implications for biomarker studies. PLoS Med Dec. 2, 2008; 5(12):e232.
Kuehn A. et al Expression analysis of kidney-specific cadherin in a wide spectrum of traditional and newly recognised renal epithelial neoplasms: diagnostic and histogenic implications. Am J Surg Pathol. Oct. 2007; 31(10):1528-33.
Laury A. R. et al. PAX8 reliably distinguishes ovarian serous tumors from malignant mesothelioma. Am J Surg Pathol 2010;34:627-635.
Laury A. R. et al. A comprehensive analysis of PAX8 expression in human epithelial tumors. Am J Surg Pathol 1011;35:816-826, (2011).
Lee A. H. et al. The expression of Wilms' tumour-1 and CA125 in invasive micropapillary carcinoma of the breast. Histaphatology Dec. 2007; 51(6):824-8.
Long K. B. et al. PAX8 Expression in well differentiated pancreatic endocrine tumors: correlation with clinicopathologic features and comparison with gastrointestinal and pulmonary carcinoid tumors. Am J Surg Pathol 2010;34:723-729.
Lorenzo P.I. et al. Immunohistochemical assessment of PAX8 expression during pancreatic islet development and in human neuroendocrine tumors. Histochem Cell Biol 2001;136:595-607.
Mazai P. R. et al. Expression of aquaporins and PAX-2 compared to CD10 and cytokeratin 7 in renal neoplasms:a tissue microarrary study. Mod Pathol, Apr. 2005:18(4):535-40.
Mazal P. R. et al. Expression of kidney-specific cadherin distinguishes chromophobe renal cell carcinoma from renal oncoctyoma. Hum. Pathol. Jan. 2005; 36(1):22-8.
Moretti L. et al. N-terminal PAX8 polyclonal antibody shows cross-reactivity with N-terminal region of PAX5 and is responsible for reports of PAX8 positivity in malignant lymphomas. Mod. Pathol. 2011.
Nonaka D. et al. Expression of PAX8 as a useful marker in distinguishing ovarian carcinomas from mammary carcinomas Am J Surg Pathol Oct. 2008; 32(10):1566-71.
Nonaka D et al. Diagnostic utility of thyroid transcription factors PAX8 and TTF-2 (FoxE1) in thyroid epithelial neoplasms. Mod Pathol. Feb. 2008; 21(2):192-200.
Ozcan A. et al. PAX 8 expression in non-neoplastic tissues, primary tumors, and metastatic tumors: a comprehensive immunohistochemical study. Mod Pathol 2001;24:751-764.
Reid-Nicholson M. et al. Immunophenotypic diversity of endometrial adenocarcinomas: implications for differential diagnosis. Mod. Pathol Aug. 2006; 19(8):1091-100.
Sangoi A. R. et al. PAX8 expression reliably distinguishes pancreatic well differentiated neuroendocrine tumors from ileal and pulmonary well-differentiated neuroendocrine tumors and pancreatic acinar cell carcinoma. Mod. Pathol 2011;24:412-424.
Tacha D. et al. Expression of PAX8 in Normal and Neoplastic Tissues: A Comprehensive Immunohistochemical Study. Appl Immun. Mol. Morph. 2011. In press doi: 10.1097/PA.0b013e3182025f66.
Tong G. X. et al. Expression of PAX8 in nephrogenic adenoma and clear cell adenocarcinoma of the lower urinary tract: evidence of related histogenesis? Am J Surg Pathol. Sep. 2008; 32(9):1380-7.
Tong G. X. et al. Expression of PAX8 in normal and neoplastic renal tissues: an immunohistochemical study. Mod. Pathol. Sep. 22, 2008(9):1218-27.
Tomos C. et al. Expression of WT1, CA 125, and GCDFP-15 as useful markers in the differential diagnosis of primary ovarian carcinomas versus metastatic breast cancer to the ovary. Am J Surg Pathol. Nov. 2005; 29(11):1482-9.
Turque N. et al. Pax-QNR/Pax-8, a paired box- and homeobox containing gene expressed in neurons, is also expressed in pancreatic endocrine cells. Mol. Endocrinol 1994;8:929-938.
Zhang, P. et al. Immunohistochemical analysis of thyroid-specific transcription factors in thyroid tumors. Pathol Int 2006;56:240-245.
Zhou M. et al. The usefullness of immunohistochemical markers in the differential diagnosis of renal neoplasms. Clin Lab Med. Jun. 25, 2005(2):247-57.
Zhu W. et al. WT1 monoclonal CEA, TTF1, and CA125 antibodies in the differential diagnosis of lung, breast and ovarian adenocarinomas in serious effusions. Diag Cytopathol Jun. 25, 2007(6):370-5.
Ye J. et al. Diagnostic utility of PAX8, TTF-1 and napsin A for discriminating metastatic carcinoma from primary adenocarcinoma of the lung. Biotech Histochem 2011.
U.S. Appl. No. 61/484,579, filed May 10, 2011, Entitled Systems and Methods for Anti-PAX8 Antibodies.
U.S. Appl. No. 61/558,035, filed Jan. 18, 2012, Entitled Anti-PAX8 Antibodies Systems and Methods.
International Application No. PCT/US2012/021317, filed Jan. 13, 2012, Writtem Opinion of the International Search Authority dated Feb. 15, 2013.
International Application No. PCT/US2012/021317, filed Jan. 13, 2012, Written Opinion of the International Searching Authority dated Feb. 15, 2013.
Tockman et al, Cancer Research vol. 52 p. 2711s (1992).
Janicke et al Fibrinolysis vol. 4 p. 69 (1990).
Paul, Fundemental Immunology, 3rd Edition, 1993, pp. 292-295.
Rudikoff et al (Proc. Natl. Acad. Sci. USA 1982 vol. 79: p. 1979).
Pascalis et al (The Journal of Immunology (2002) 169,3076-3084).
Brown et al. (J. Immunol. May 1996; 156(9):3285-3291.
Casset et al. (2003) BBRC 307, 198-205.
Vajdos et al (J. Mol. Biol. Jul. 5, 2002;320(2); 415-428).
Parent U.S. Appl. No. 14/004,400, filed Sep. 19, 2013.
Anonymous: "Double vision, The double stain, polymer detection system", Biocare Medical, Oct. 2, 2003, pp. 1-3, XP002667410, retrieved from the Internet: URL:htt12 ://web/archive .org/web/20031 002060452/httQ ://biocare. net/Detection. htm [retrieved Jan. 18, 2012).
Anonymous: "Double vision, The double stain, polymer detection system", Biocare Medical, Jan. 1, 2004, pp. 1-5, XP002667411, retrieved from the Internet: URL: htt12 ://web/archive .org/web/20040 1 01180833/httQ :1/biocare. net/Detection. htm [retrieved Jan. 18, 2012].
Susan Van Noorden., "Immunocytochemistry for light microscopy a technical update", The biomedical Scientist, XP-002522654, Aug. 2003, pp. 808-811.
Rami Suzuki. et al., "Proliferation and differentiation in the human breast during pregnancy", Differentiation. vol. 66, No. 2-3, XP-002522647, Oct. 2000, pp. 106-115.
DAKO datasheet, DuoFlex Cocktail, Code IC004 (119877-001), (2008).
BioGenex datasheet, Rabbit Anti-PIN4 Cocktail—AB448ME, Doc. No. 932-448ME Rev A, release date Aug. 17, 2007.
van der Loos, "Immunoenzyme Multiple Staining Methods", Microscopy Handbooks 45, (1999); Bios Scientific Publishers Ltd: Oxford, UK.
Hiromichi Tsurui, et al., "Seven-color Fluorescence Imaging of Tissue Samples Based on Fourier Spectroscopy and Singular Value Decomposition", The Journal of Histochemistry & Cytochemistry, vol. 48, No. 5, XP-002522648, May 2000, pp. 653-662.
David Y. Mason, et al., "Double immunofluorescence labelling of routinely processed paraffin sections", Journal of Pathology, vol. 191, No. 4. XP-002522649, Aug. 2000, pp. 452-461.
Susan Van Noorden., "Advances in immunocytochemistry", Folia Histochemica Et Cytobiologica, vol. 40, No. 2, XP-008104795, 2002, pp. 121-124.
Van der Loos, et al., "Immunohistochemical Detection of Interferon-y: Fake or Fact?", The Journal of Histochemistry & Cytochemistry, vol. 49, No. 6, XP-002522653, Jun. 2001. pp. 699-709.

(56) References Cited

OTHER PUBLICATIONS

Van der loos. et al. "The Animal Research Kit (ARK} Can Be Used in a Multistep Double Staining Method for Human Tissue Specimens", The Journal of Histochemistry & Cytochemistry, vol. 48, (10}: 1431-1437 (2000).
Van der Loos, et al, "Multiple immunoenzyme staining techniques Use of fluoresceinated, biotinylated and unlabeled monoclonal antibodies", Journal of Immunological Methods, 117 (1989), pp. 45-52.
Van der loos. et al. "An Immunoenzyme Triple-staining Method Using Both Polyclonal and Monoclonal antibodies from the same Species. Application of combined direct, Indirect, and Avidin-Biotin Complex (ABC) Technique", The Journal of Histochemistry and Cytochemistry, vol. 35, No. 11, pp. 1199-1204 (1987).
Van der Loos, et al. "Practical suggestions for successful immunoenzyme double-staining experiments", Histochemical Journal (25), pp. 1-13 (1993).
Brunangelo Falini, et al., "Double Labeled-Antigen Method for Demonstration of Intracellular Antigens in Paraffin-embedded Tissues", The Journal of Histochemistry and Cytochemistry. vol. 30, No. 1, pp. 21-26 (1982).
Data Sheet Fast Red Stubsrate Pack and Compponents for Use with Alakline Phosphatase Detection Kits & BioGenex Automated Staining Systems (Doc. No. HK180, Rev. No. F112) Jul. 1, 2003 accessed from web.archive.org/web/20030701115828/http://www.bioQenex.com/bioQenex h.html.
Vector Red Alkaline Phosphatase Substrate Kit I Cat. No. SK-5100, Oct. 31, 2000, accessed from web.archive.org/web/20031202200453/http://www.vector.labs.com/protocols.asp.
Cordell et al, Journal of Histochemistry and Cytochemistry, 1984, vol. 32, No. 2 pp. 219-229 attached online version htte://jhc.sageeub.com/content/32/2/219.
Instructions for Universal Alkaline Phosphatase Immunostaining Kit (For Mouse and Rabbit Primary Antibodies) Cat. #KA-50F Apr. 7, 2003 Accessed from web.archive.org/web/20030407222427/http:I/dbiosys.com/new/index.asp?fuse=dsp cat&id=5.
Elias, Immunohistopathology—A Practical Approach to Diagnosis, 2nd Ed., American Society for Clinical Pathology Press: Chicago, © 2003, p. 36.
U.S. Appl. No. 61/618,279, filed Mar. 30, 2012; entitled Systems and Methods for Anti-Uroplakin III Antibodies.
Molinie, V. et al., Mod. Pathol., 2004, 17, 1180.
Paner, GP,. et al., Best Prac. In Diag. Immunohist.: Prostate, 2008, 132, 1388.
Rubin, MA et al., JAMA, 2002, 287, 1662.
Shah, RB et al., Am. J. Surg. Path., 2002, 26, 1161.
Signoretti, Sabina 'p63 is a prostate basal cell marker and is required for prostate development'. Am J Pathol, vol. 157, No. 6, Dec. 2000, 1769-75.
Tacha, DE and Miller, RT, Appl. Immunohistochem. Mol. Morph.. 2004, 12, 75.
Tavora. F and Epstein, JI, Am. J. Surg. Path., 2008, 32, 1060.
Yang, Yet. al., Am. J. Path, 1997, 150, 693.
Abrahams, NA, et. a f., Histopathology, 2002, 41, 35.
Adley, BP et al., Am. J. Clin. Path., 2006, 126, 849.
Beach, R et al., Am. J. Surg. Path., 2002, 26, 1588.
Bostwick, DG and Qian, J., Mod. Pathol., 2004, 17, 360.
DAKO Press Release Sep. 14, 2009, New Duoflex Cocktail Antibodies.
DAKO Screen Shot DuoFlex Cocktail, Anti-AMACR, Anti-Cytokeratin HMW, Anti-Cytoderatin 5/6: Oct. 5, 2009.
Herawi, M and Epstein, JI, Am. J. Surg. Path., 2007, 31, 889.
Jiang, Z et al., Am. J. Clin. Path., 2004, 122, 275.
Jiang, Z et al., Am. J. Clin. Path., 2005, 123, 231.
Jiang, Z et al., Am. J. Surg. Path., 2001, 25, 1397.
Luo, J et. al., Cancer. Res., 2002, 62, 2220.
Reis-Filho et al, Virchows Arch. (2003) vol. 443, pp. 122-132.
12 pages from catalog: "product information form the Sigma-Aldrich Online Catalog" at sigmaaldrich.com/ .. ./ProductDetail.do?I . . . accessed Feb. 14, 2011.
8 pages from catalog: "product information form the Sigma-Aldrich Online Catalog" at sigmaaldrich.com/ .. ./ProductDetail.do?I . . . accessed Feb. 16, 2011.
Epstein, JI, and Netto, GJ., Biopsy interpretation of the prostate, 2008, Lippincott, Williams & Wilkins: Philadelphia, p. 99.
BioSB p40 IHC of p40 on an FFPE Prostate Tissue, http://www.biosb.com/p40-page, Jul. 29, 2015, 4 pages.
Zeta Corporation IVD Data Sheet (Rev 052014) p40 (Clone ZR8), 7 pages, (2014).
U.S. Appl. No. 61/770,956 entitled "Systems and Methods for Anti-p40 Antibodies" filed Feb. 28, 2013.
European Patent App. No. 14178215.1 Examination Report dated Dec. 15, 2015, 5 pages.
European Patent App. No. 14178215.1 Search Report dated Dec. 1, 2014, 11 pages.
Cartron, et al. Therapeutic activity of humanized anti-DC20 monoclonal antibody and polymorphism in IgG Fc receptor gene. www.bloodjournal.org, Jan. 21, 2016. 6 pages.
Creative Biolabs, Chimeric IgG construction; (c) 2007-2016 Creative Biolabs, 2 pages.
Foran, James M. et al. European Phase II Study of Rituximab (Chimeric Anti-CD20 Monoclonal Antibody) for Patients with Newly Diagnosed Mantle-Cell Lymphoma and Previously Treated Mantle-Cell Lymphoma, Immunocytoma, and Small B-Cell Lymphocytic Lymphoma. Journal of Clinical Oncology, vol. 18, No. 2/317; Jan. 1, 2000, 7 pages.
Eng, Hui-Yan, et al. Enhanced antigen detection in immunohistochemical staining using a 'digitized' chimeric antibody. Oxford, Protein Engineering, Design & Selection, 2016, vol. 29 No. 1, pp. 11-21. Sep. 25, 2015, 11 pages.
Carter, Paul J. Potent antibody therapeutics by design. Nature Reviews, Immunology. vol. 6, May 2006. pp. 343-357. 15 pages.
Chames et al. Therapeutic antibodies: success, limitations and hopes for the future. Themed Section: Vector Design and Drug Delivery Review. British Journal of Pharmacology (2009) 157,200-233.
Jakobovits, Aya. Production of fully human antibodies by transgenic mice. Cell Genesys Inc., Foster City, USA. Current Opinion in Biotechnology 1995, 6:561-566.
Kellermann & Green, Antibody discovery: the use of transgenic mice to generate human monoclonal antibodies for therapeutics. Current Opinion in Biotechnology 2002, 13:593-597.
Morrison et al. Chimeric human antibody molecules: Mouse antigen-binding domains with human constant region domains. Proc. Natl. Adad. Sci. USA. vol. 81, pp. 6851-6855, Nov. 1984.
Winter et al. Humanized antibodies. Immunology Today vol. 14 No. 6 1993. 4 pages.
U.S. Appl. No. 15/026,904, filed Apr. 1, 2016. First Inventor: David Tacha.

* cited by examiner

SEQUENCE LISTING

```
<160> NUMBER OF SEQ ID NOS: 3

<210> SEQ ID NO 1
<211> LENGTH: 662
<212> TYPE: DNA
<213> ORGANISM: Mus musculus

<400> SEQUENCE: 1
gtaacggccg ccagtgtgct ggaattcggc ttcccttgac caggcatccc agggtcacca     60
tggagttagt ttgggcagca gatccagggg tcagtggata gacagatggg ggtgtcgttt    120
tggctgcaga gacagtgacc agagtccctt ggccccagta agcaaacccc ccatagtctt    180
tatgtcttga acagtaatac atggccgtgt cctcagactt cagactgctc atttgcaggt    240
acagggtgtt cttggcattg tctctggaga tggtgaatcg gccctttaca gtgtctggag    300
agtaggtgtt accaccacca ttactaatgt atgcgaccca ctccagcctc ttgtctggag    360
tctggcgaac ccaagacatg gtatagctac tgaaagtgaa tccagaggct gcacaggaga    420
gtttcaggga ccctcctggc tgcactaaat ctcccccaga ctccaccagc ttcacttcac    480
acaggacacc ttttaaaaca aggacaagga aaaccaagct gagcccaaag tcctaaatct    540
cccccagact ccaccagctt cacttcacac agacaccttt taaacaagg acaaggaaaa    600 ccaagctgag cccaaagtcc ataagccgaa ttctgcagat atccatcaca ctggcggccg    660
ct                                                                    662

<210> SEQ ID NO 2
<211> LENGTH: 595
<212> TYPE: DNA
<213> ORGANISM: Mus musculus

<400> SEQUENCE: 2
gtaacggccg ccagtgtgct ggaattcggc ttctcactgg atggtgggaa gatggataca     60
gttggtgcag catcagcccg tttatttcc aactttgtcc ccgagccgaa cgtgattgga    120
tactctacaa gttgttgaca gtaatacaca cccacatcct cagccttcac tctactgatt    180
tccagggtga aatctgttcc tgacccactg ccactaaacc ggtctgagac tcctgatgca    240
cgggtggaca tcaaatagat caggagctga ggagattgtc ctggtctctg cagaaaccaa    300
ttcaagtacg tcttcccatc cttatatagg agactcttag tagacctgca ggagatggaa    360
actgattctc cagaagtgac aggattggag agttcatcct gggttatcac aatatcccca    420
ctgactccag agatccagaa cataagcaac cccaggacct gagtgagcac actcataagc    480
cgaattctgc agatatccat cacactggcg gccgctcgag catgcatcta gagggcccaa    540
ttcgccctat agtgagtcgt attacaattc actggccgtc gttttacaac gtcgt         595
```

```
<210> SEQ ID NO 3
<211> LENGTH: 15
<212> TYPE: PRT
<213> ORGANISM: Homo sapiens

<400> SEQUENCE: 3

Glu Gln Gly Leu Tyr Pro Leu Pro Leu Leu Asn Ser Thr Leu Asp
1               5                   10                  15
```

SYSTEMS AND METHODS FOR ANTI-PAX8 ANTIBODIES

PRIORITY CLAIM

This application is a continuation of U.S. application Ser. No. 14/004,400 filed Sep. 19, 2013 which is the United States National Phase of International Patent Application Number PCT/US2012/037367 filed May 10, 2012 which claims priority to and the benefit of U.S. Provisional Application No. 61/484,579 filed May 10, 2011 and U.S. Provisional Application No. 61/588,035 filed Jan. 18, 2012, each application hereby incorporated by reference herein in their entirety.

TECHNICAL FIELD

This invention relates to novel PAX8 antibodies, compositions, and kits comprising the antibodies and methods for using the antibodies.

BACKGROUND OF THE INVENTION

Microscopic examination of tissue samples, particularly those obtained by biopsy, is a common method for diagnosis of disease. In particular, immunohistochemistry (IHC), a technique in which specific antibodies are used to detect expression of specific proteins in the tissue sample, is a valuable tool for diagnosis, particularly for the detection and diagnosis of cancer.

The paired box (PAX) genes are a family of cell-lineage transcription factors that may play fundamental roles during organogenesis and are regulatory proteins expressed in normal and neoplastic cells of the same lineage. PAX8 is a nephric-lineage transcription factor that may be a crucial transcription factor for organogenesis of the thyroid gland, kidney and Müllerian system. These proteins are required for cell growth and differentiation in embryonic tissues and can be expressed in adult tissues and in specific cell-lineage neoplastic tissues.

PAX8 may have been shown to be a useful marker of several cancers, particularly kidney, ovarian, endometrial, and thyroid cancers. Detection of PAX8 by anti-PAX8 antibodies, using immunohistochemistry, may have been shown to be a valuable tool for detection and diagnosis of these cancers.

Immunohistochemical detection of PAX8 expression may be advantageous for several reasons: PAX8 may be present in a high percentage of cases of these cancers; PAX8 can identify both primary and metastatic tumors of these types; and even nuclear expression of PAX8 may result in strong staining of the nucleus, which may ease interpretation and diagnosis.

Unfortunately, some known anti-PAX8 antibodies useful for immunohistochemistry may have the disadvantage that they cross-react with lymphocytes, particularly B-cells, which may frequently infiltrate into the site of a tumor. Simultaneous staining of B-cells, alongside positive staining of PAX8, can complicate analysis and even interpretation of the tissue sample. In such cases, the pathologist may have to rely on other methods (e.g., morphological differences) to discriminate B-cell staining from tumor cells. Furthermore, staining of B-cells can be a significant disadvantage in the analysis of tissue samples from lymph nodes, a common scenario when evaluating the potential of metastasis into a lymph node. Considering that lymph nodes may naturally contain large numbers of B-cells, staining a lymph node sample with one of the currently known PAX8 antibodies may result in extensive staining of B-cells and may make identification of metastatic tumor cells in the lymph node extremely difficult. A more specific anti-PAX8 antibody that does not cross-react and stain B-cells could offer a significant advantage by simplifying interpretation, resulting in clearer, more confident and even accurate diagnosis.

DISCLOSURE OF THE INVENTION

General embodiments of the present invention may include monoclonal antibodies for recognizing PAX8, methods for their preparation, use in immunohistochemistry, and the like. This mouse monoclonal anti-PAX8 antibody [BC12] may be useful for the detection of PAX8 in tissue samples, perhaps with several significant, but unexpected advantages over currently known PAX8 antibodies. When used in traditional immunohistochemistry procedures, the mouse PAX8 antibody [BC12] may result in nuclear staining of PAX8 with a sensitivity perhaps similar to that of known PAX8 antibodies. However, BC12 may exhibit increased specificity, perhaps as compared to past PAX8 antibodies, which may offer significant improvements. In contrast to known PAX8 antibodies, the present invention's mouse PAX8 antibody [BC12] may not stain B-cells. As a result, BC12 may offer a considerable advantage for diagnosis, since the interpretation of the sample may not be complicated by staining of infiltrating B-cells. With BC12, analysis of the sample may be simplified and PAX8 expression in tumor cells may be readily identifiable. Furthermore, evaluating the presence of metastatic tumor cells in lymph node samples may be uncomplicated and straightforward when using BC12, as BC12 may avoid the complications associated with staining of the B-cells that may be naturally present in the lymph node.

Furthermore, BC12 may not stain normal or neoplastic pancreatic tissue and neuroendocrine cells in normal stomach. A common feature of past PAX8 antibodies may be the staining of normal pancreatic tissue and some cases of pancreatic cancer and in some cases, neuroendocrine cells in the stomach. Such additional reactivity and lack of specificity, can lead to ambiguity in diagnosis, particularly in cases of metastatic disease, where the primary tumor may be unknown. The increased specificity of BC12 resulting from the lack of cross-reactivity and staining of pancreatic tissue and certain neuroendocrine cells may be an advantage for its use, leading to less ambiguous, more confident diagnosis.

Naturally, further objects, goals and embodiments of the invention(s) are disclosed throughout other areas of the specification, claims, and drawings.

MODE(S) FOR CARRYING OUT THE INVENTION

Figure 1:
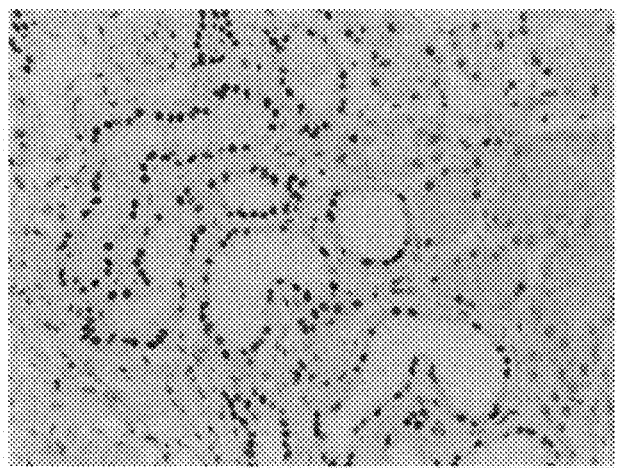
FIG. 1 shows an example of PAX8 staining on kidney tissue with PAX8 Mouse Monoclonal [BC12] at 20×.
Figure 2:
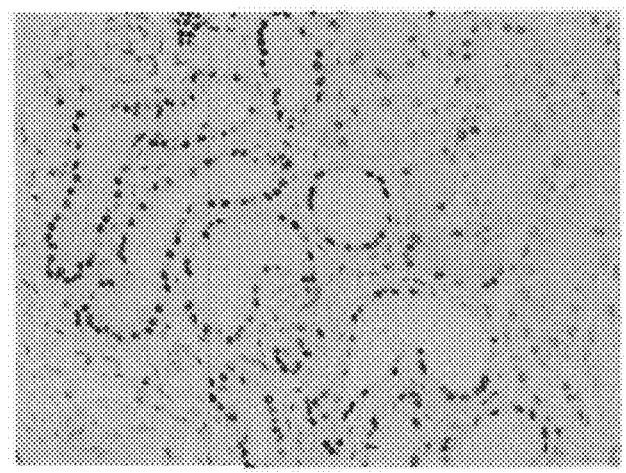
FIG. 2 shows an example of PAX8 staining on kidney tissue with PAX8 Rabbit Polyclonal at 20×.
Figure 3:
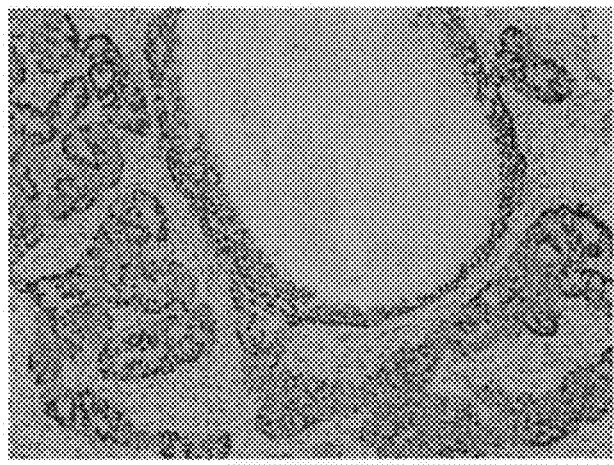
FIG. 3 shows an example of PAX8 staining on Ovarian Cancer tissue with PAX8 Mouse Monoclonal [BC12] at 10×.
Figure 4:
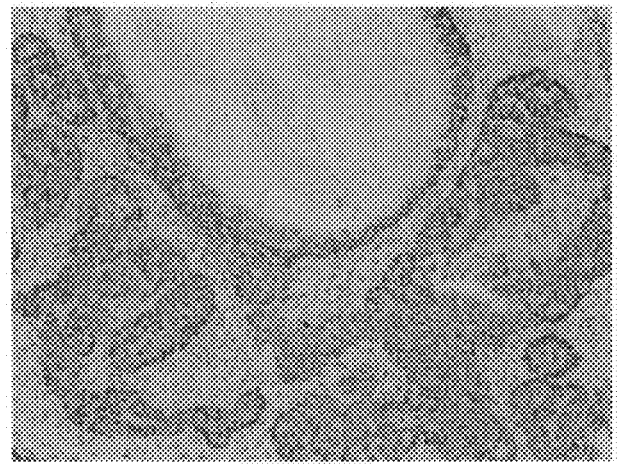
FIG. 4 shows an example of PAX8 staining on Ovarian Cancer tissue with PAX8 Rabbit Polyclonal at 10×.
Figure 5:
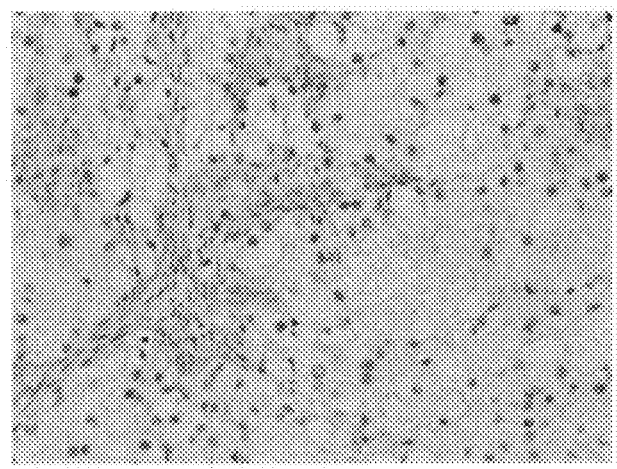
FIG. 5 shows an example of PAX8 staining on a Clear Cell Renal Carcinoma with PAX8 Mouse Monoclonal [BC12] at 20×.
Figure 6:
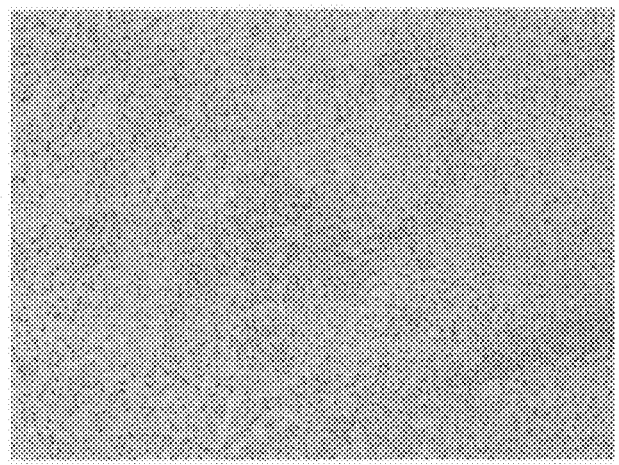
FIG. 6 shows an example of PAX8 staining using PAX8 Mouse Monoclonal [BC12] on Tonsil at 10× and having no stain on the B-cells.
Figure 7:
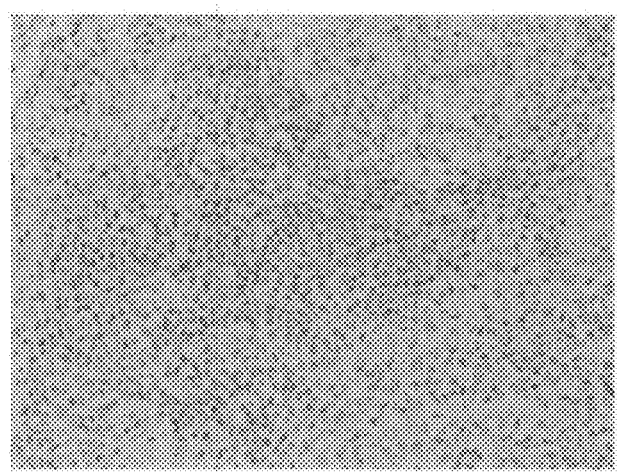
FIG. 7 shows an example of PAX8 staining using PAX8 Mouse Monoclonal [BC12] on Tonsil at 20× and having no stain on the B-cells.
Figure 8:
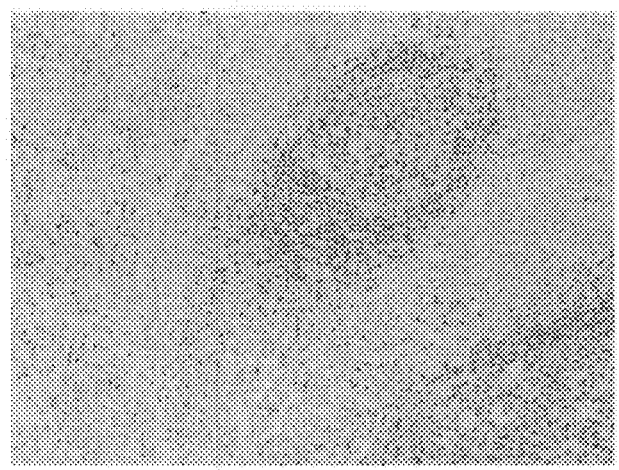
FIG. 8 shows an example of PAX8 staining using PAX8 Rabbit Polyclonal on Tonsil at 10× wherein staining of B-cells is present.
Figure 9:
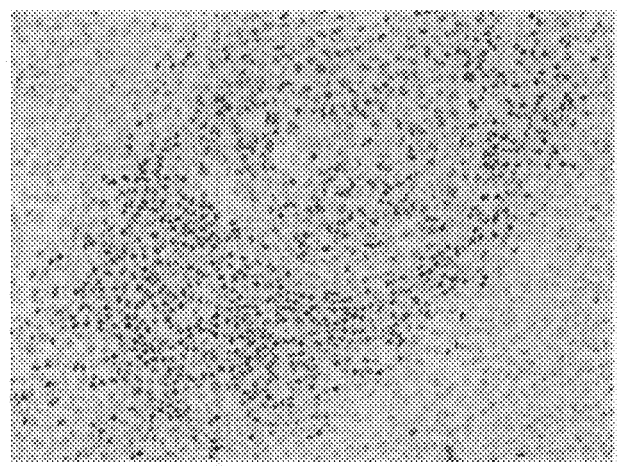
FIG. 9 shows an example of PAX8 staining using PAX8 Rabbit Polyclonal on Tonsil cells at 20× wherein staining of B-cells is present.
Figure 10:
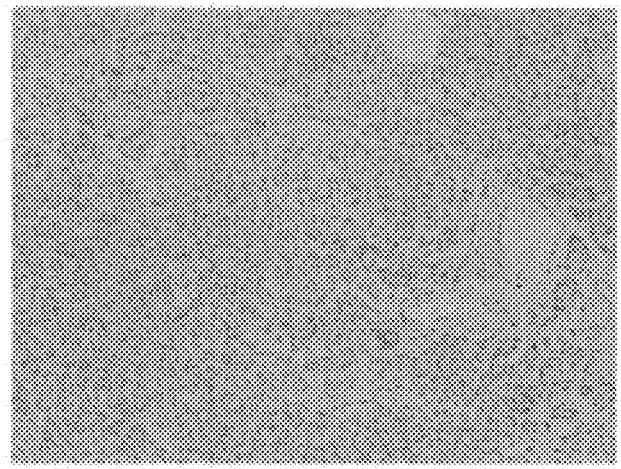
FIG. 10 shows an example of PAX8 staining using PAX8 Mouse Monoclonal [BC12] on pancreas tissue at 10× wherein no stain is present.
Figure 11:
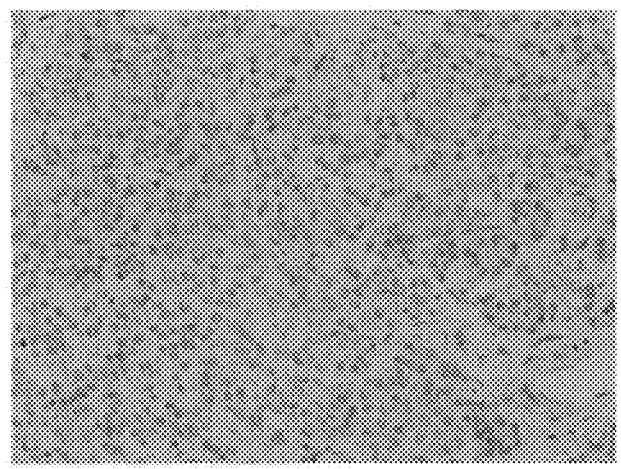
FIG. 11 shows an example of PAX8 staining using PAX8 Mouse Monoclonal [BC12] on pancreas tissue at 20× wherein no stain is present.
Figure 12:
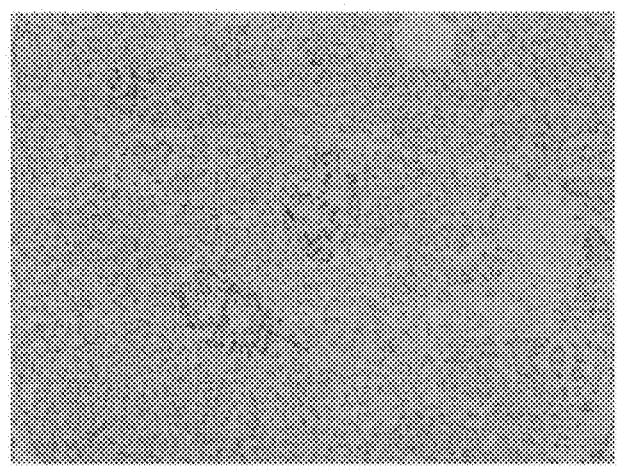
FIG. 12 shows an example of PAX8 staining using PAX8 Rabbit Polyclonal on pancreas tissue at 10× wherein stain is present.
Figure 13:
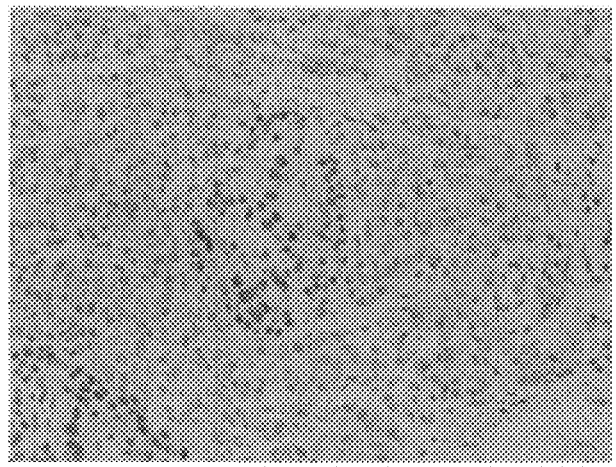
FIG. 13 shows an example of PAX8 staining using PAX8 Rabbit Polyclonal on pancreas tissue (islets of Langerhans) at 20× wherein stain is present.

As may be understood from the earlier discussion, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Embodiments of the present invention may provide antibodies, monoclonal antibodies, any fragments thereof such as antigen binding fragments thereof, and methods thereof that specifically bind to PAX8 and may be used for the detection of PAX8 in the detection, diagnosis, prognosis, prediction of outcome of treatment, assessment of efficacy, assessment of recurrence, or the like for several types of cancers. The monoclonal antibody may be an antibody fragment, a mouse monoclonal antibody, a humanized monoclonal antibody, a human monoclonal antibody, an antibody conjugated with a label, an antibody labeled with a detectable signal or stain, an antibody labeled with a toxin, or the like. Examples of labels may include but are not limited to radioactive element, magnetic particles, radioisotope, fluorescent dye, enzyme, toxin, signal, stain, any combination thereof, or the like. Systems and methods of the present invention may relate to the monoclonal antibody or its antigen binding portion capable of binding to PAX8. In other embodiments, the present invention may provide a monoclonal antibody or its antigen binding portion thereof capable of binding to PAX8 but which does not bind to B-cells.

Mouse monoclonal antibodies may be commonly used in immunoassay methods to identify specific analytes, including as primary antibodies in immunohistochemistry procedures. Mouse monoclonal antibodies specific for the protein target of interest can typically be produced using generally known procedures. Generally, exposing a mouse to the antigen of interest (e.g. a peptide fragment of the desired target or the full-length protein target) may induce an immune response in which the mouse generates multiple antibodies that bind the antigen, each of which may be produced by a particular B-cell. These B-cells may be isolated from the mouse spleen and the antibodies produced may be evaluated for their suitability as primary antibodies in IHC. After selecting the optimal antibody, the associated B-cell may be fused with a tumor cell using known procedures, perhaps resulting in a hybridoma, a new cell line that can endlessly replicate and may continuously produce the desired antibody.

Monoclonal antibodies may be preferred over polyclonal antibodies for several reasons. In particular, monoclonal antibodies may be derived from a single B-cell and as such may recognize a single epitope, perhaps resulting in greater specificity. Monoclonal antibodies may also be conveniently and reproducibly generated in cell culture, perhaps resulting in a constant supply of the desired antibody. In embodiments a monoclonal antibody may include but is not limited to an isolated monoclonal antibody, a mouse monoclonal antibody, a rabbit monoclonal antibody, a goat monoclonal antibody, a horse monoclonal antibody, a chicken monoclonal antibody, a humanized monoclonal antibody, a chimeric antibody, and any combination thereof, or the like.

Embodiments of the present invention may provide a kit (5) and methods of using such kit which may be a diagnostic or prognostic kit that includes an antibody or fragment thereof or even portion thereof as discussed herein with perhaps an antibody detection element of the antibody, fragment, or portion thereof when bound to an antigen where a biological sample (2) may be contacted with the antibody, fragment, or portion thereof and detection of the bound antibody-antigen may be determined. A biological sample may include but is not limited to a normal tissue, neoplastic tissue, kidney tissue, ovarian tissue, thyroid tissue, endometrial tissue, renal tissue, tonsil tissue, pancreas tissue, colon tissue, lymph node tissue, neoplastic pancreatic tissue, stomach tissue, bladder tissue, prostate tissue, lung tissue, breast tissue, or the like. As discussed herein, use of the antibody or fragment thereof or portion thereof or composition may performed on an automated staining device such as with methods including but not limited to immunoassay, immunohistochemistry (IHC), IHC of FFPE, ICH of frozen-tissue sections, and ELISA. In embodiments, detection of the antibody-antigen binding may be made manually, automatically, via image analysis or the like and may even be made via an automated staining device.

Figure 33:
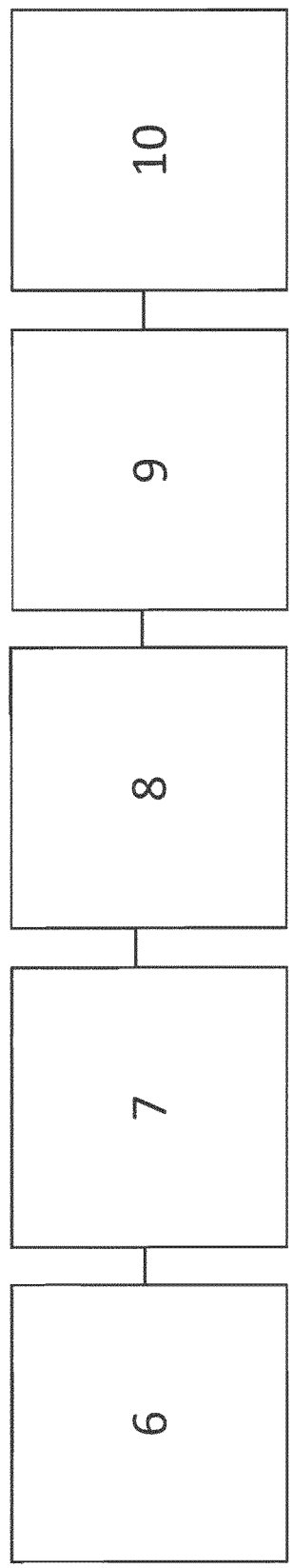
FIG. 33 shows an example of a schematic summary of an immunoassay method in accordance with various embodiments of the present invention.

As but one example of an immunoassay method, embodiments of the present invention may provide obtaining tissue from an animal or human to be tested (6), fixing or freezing said tissue (7), treating said fixed or frozen tissue to unmask epitopes to PAX8 (8), contacting said treated tissue with an antibody or fragment thereof as discussed herein in an amount and under conditions such that said antibody or fragment thereof binds to a PAX8 protein if said protein is present in said tissue (9); and perhaps even detecting the presences of said bound antibodies (10), as schematically represented in FIG. 33.

Figure 32:
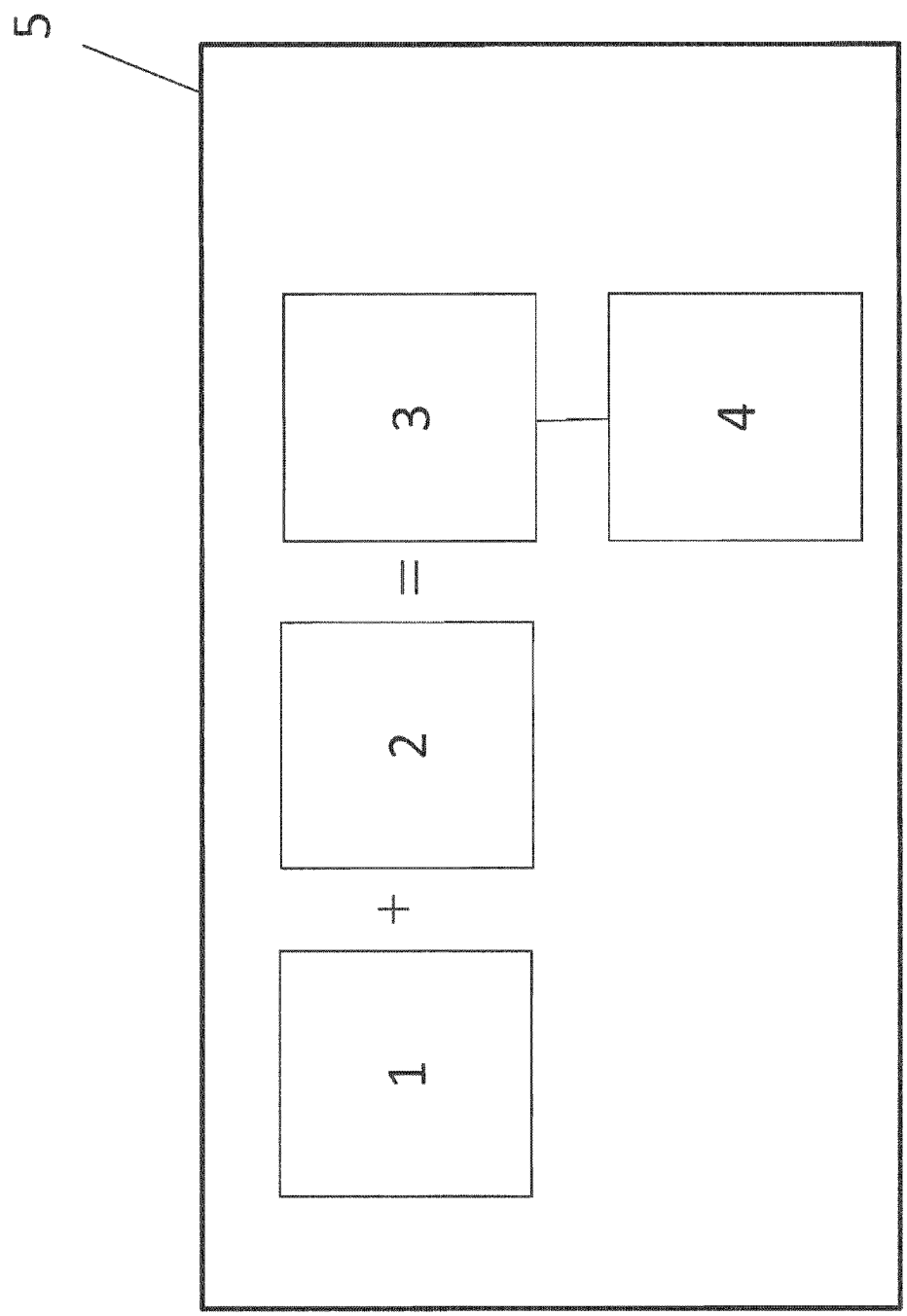
FIG. 32 shows an example of a schematic summary of a kit in accordance with various embodiments of the present invention.

FIG. 32 shows a schematic summary of various embodiments of the present invention including a kit (5) which may provide an antibody, fragment thereof, portion thereof, in a composition or even in a cocktail (1), perhaps even provided from a hybridoma, the antibody (1) or the like may be contact with a biological sample (2) to form at least one antibody-antigen complex (3) which may then be detected with a detector (4).

In embodiments, the PAX8 antibody clone BC12 can be obtained by immunizing Balb/C mice with a full length human PAX8 recombinant protein obtained by E. coli expression. The PAX8 proteins may be injected into the BALB/c mice, with an adjuvant, via subcutaneous and intraperitoneal injections alternatively, about 5 times at about three week intervals. The immune reactivity to PAX8 may be assessed by direct ELISA on recombinant PAX8 protein. Mice with the highest titer may be chosen for developing hybridomas by cell fusion. A hybridoma clone demonstrating the best reactivity to PAX8 on human tissues may be chosen and may be designated as BC12. The BC12 clone may be tested for isotype and may be identified as a mouse IgG1/kappa. The BC12 antibody may be produced by large scale tissue culture of the hybridoma cells and by ascites in BALB/c mice. The supernatant and antibody ascites may be collected and the antibody may be purified by Protein A affinity column. BC12 demonstrated specific reactivates to human PAX8 protein by ELISA, Western blotting, and even human tissues.

Mouse monoclonal anti-PAX8 antibody [BC12] may be produced using these general procedures and may be evaluated by immunohistochemistry for sensitivity and specificity on a variety of normal and neoplastic tissues, particularly in comparison to the previously known rabbit polyclonal PAX8 antibody that is widely used.

Example of PAX8 Protein Expression:

A full-length PAX8 recombinant protein may be cloned and expressed from E. Coli. Briefly, PAX8 cDNA may be cloned and purified. The PAX8 cDNA may be digested by restriction enzymes and ligated into the pET30a-GST vector. BL21 cells may be transformed with the construct. The colonies expressing the correct size of recombinant protein may be selected and sequenced. A further scale up production may be performed by culturing the E. coli in LB media containing 0.5 mM IPTG. The final PAX8 recombinant protein may be purified and analyzed by SDS-PAGE.

Example of Host Immunization:

Female BALB/c (about 6 to about 8 weeks old) mice may be immunized intraperitoneally (i.p.) with about 100 µg human PAX8 protein per mouse in complete Freund's adjuvant. About three weeks later, the mice may be boosted with another 100 µg human PAX8 per mouse in incomplete Freund's adjuvant about 4 more times in about 3 week intervals. Mice may be bled from the tails, and sera may be collected and stored at −20° C. for later analysis of antibody titers by enzyme-linked immunosorbent assay (ELISA).

Example of Hybridomas:

Hybridomas producing antibodies to PAX8 may be generated by standard techniques from splenocytes of PAX8-immunized BALB/c mice. Briefly, splenocytes from PAX8-immunized mice may be fused to P3-X63-Ag 8.653 myeloma cells (non-secreting myeloma derived from SP2/0 Balb/c myeloma cells) by incubation with about 50% polyethylene glycol at a ratio of about 4:1. Following incubation, cells may be pelleted by centrifugation at about 3000×g for about 10 minutes, washed in about 25 ml of PBS, recentrifuged, and cell pellet may be resuspended in about 100 ml of fresh Dulbecco's Medium containing about 20% fetal bovine serum (Hyclone, Utah, Co). Aliquots of about 100 µl can be added to each well of ten 96-well microtiter plates (Corning, Lowell, Mass.). About twenty four hours later, about 100 µl DMEM culture medium supplemented with about 1M hypoxanthine (HT), about 4 mM aminopterin and about 160 mM thymidine (HAT) can be added to each microtiter well. Media may be replaced after about 4 days with complete media (perhaps containing HAT and HT). Over the following about 10 days, media may be removed and replaced with fresh media with reduced or perhaps even no HAT and HT added. Hybridoma supernatants may be screened by ELISA for antibody reactivity to PAX8, and hybridoma clones may then be selected and stabilized by cloning twice by limiting dilution.

Hybridoma cells referred to as Anti PAX8 Mouse hybridoma clone BC12 Lot: 042811 have been deposited at American Type Culture Collection (ATCC) in Manassas, Va. on May 4, 2011 and the he deposit received ATCC Patent Deposit Designation No. PTA-11873.

ELISA:

Host anti-sera immune responses to PAX8 may be measured by ELISA. Briefly, a solution of PAX8 (1 µg/ml) in phosphate-buffered saline (PBS) may be used to coat 96-well flat bottom polystyrene plates. The plates may then be blocked with about 1% bovine serum albumin (BSA)-PBS. Either diluted immune sera or hybridoma supernatants may be added and incubated at about 37° C. for about 1 hour. After washing the plates with PBS, the plates may be incubated with goat anti mouse-HRP reagents (Jackson Labs). Incubations may be done at about 37° C. for about 30 minutes. ABTS substrate may be added to develop color and the absorbance at about 405 nm (A405) may be measured in a microtiter plate reader.

Isotype of Monoclonal Antibodies:

The BC12 monoclonal antibody may be isotyped using a mouse monoclonal antibody isotyping kit (Invitrogen, Carlsbad Calif.). Briefly, about 100 µl of supernatant from mouse monoclonal antibody [BC12] cells may be added to the plate coated goat anti mouse IgG1, IgG2A, IgG2B, IgG3, IgM, and IgA. After about 30 minutes incubation, the plate may be washed 3 times with PBS and may be incubated with goat anti mouse Ig-HRP reagent. ABTS substrate may be added to develop color and the absorbance at about 405 nm (A405) may be measured in a microtiter plate reader.

Antibody Production and Purification:

The selected hybridoma cells from clone BC12 may be cultured with DMEM culture medium supplemented with about 10% FBS. The culture supernatants may be further purified by protein A affinity column. The hybridoma cells may also be injected into pristane-primed BALB/c mice to produce antibody ascites. The antibody ascites may be further purified by protein A affinity column. IgG concentration may be measured spectrophotometrically using the extinction coefficient for human IgG of about 1.4 (about 0.1% at about 280 nm). The purity of IgG may be determined by SDS-PAGE.

Western Blotting:

The purified monoclonal antibody [BC12] may be characterized by Western Blotting. Whole-cell lysates may be generated from OVCAR3, HEK293 cells with lysis buffer (about 1% NP40, about 0.5% sodium deoxycholate, and about 0.1% SDS in PBS) in the presence of protease inhibitors. Lysate (between about 20 and about 30 µg/lane) was subjected to protein gel electrophoresis using about 4 to about 12% SDS-PAGE with Tris-glycine buffer and may be transferred onto nitrocellulose filters in Tris-glycine buffer. Proteins on the blots may be visualized by incubating BC12 antibody for about 60 minutes in room temperature after blocking with blocking buffer, followed by incubating with peroxidase-conjugated goat anti-mouse immnoglobulins.

Determination of VH and VL Sequences:

Total RNA may be extracted from hybridomas using Qiagen kit (USA, Gaithersburg, Md.) as per the manufacturer's instructions. First-round RT-PCR may be carried out with QIAGEN® OneStep RT-PCR Kit. RT-PCR may be performed with primer sets specific for the heavy and light chains. For each RNA sample, about 12 individual heavy chain and about 11 light chain RT-PCR reactions can be set up using degenerate forward primer mixtures covering the leader sequences of variable regions. Reverse primers may be located in the constant regions of heavy and light chains. No restriction sites may be engineered into the primers. The RT-PCR products from the first-round reactions may be amplified in the second-round PCR. About 12 individual heavy chain and about 11 light chain RT-PCR reactions can be set up using semi-nested primer sets specific for antibody variable regions. The amplified cDNAs can be gel purified and may then be sequenced.

[BC12] Variable Domains were sequenced to provide isolated polynucleotides that comprise nucleic acid sequences encoding the amino acid sequences of one or more of the CDRs of the light and/or heavy chain variable regions of a monoclonal antibody described herein that binds to the PAX8 EQGLYPLPLLNSTLD epitope identified as SEQ ID NO: 3.

The sequence of the variable region of the heavy chain is identified as SEQ ID NO: 1 and the sequence of the variable region of the light chain is identified as SEQ ID NO: 2.

Therefore, embodiments of the present invention may provide a hybridoma, antibodies or fragments thereof or even portions thereof produced by the hybridoma deposited with the ATCC under ATCC Patent Deposit Designation No. PTA-11873. As discussed herein, a method for producing a monoclonal antibody from the hybridoma may include culturing a hybridoma which produces a monoclonal antibody capable of specifically recognizing PAX8; and perhaps even allowing said hybridoma to produce the monoclonal antibody. Other embodiments may include providing an antibody which has a binding specificity of PAX8 and which does not bind to B-cells. Alternatively, an antibody or fragment thereof may have a polypeptide of the amino acid sequence encoded by the nucleic acid sequence of SEQ ID NO: 1 and/or SEQ ID NO: 2. Embodiments may include an antibody or fragment thereof that specifically binds to at least one polypeptide with an amino acid sequence of SEQ ID NO:3. Even yet, an antibody may include an amino acid sequence which may be at least about 70% identical to an amino acid sequence encoded by a nucleic acid sequence of SEQ ID NO: 1 and/or SEQ ID NO: 2. In other embodiments, an isolated and purified nucleic acid sequence may include a nucleic acid sequence that may be at least about 70% identical to SEQ ID NO: 1 and/or SEQ ID NO: 2. Alternatively, an antibody or fragment thereof may be provided that specifically binds to at least one polypeptide with an amino acid sequence that may be at least 70% identical to residues of SEQ ID NO: 3 This may provide that either SEQ ID NO:1, SEQ ID NO:2, or perhaps even SEQ ID NO:3 may be modified in some way (e.g., change a few residues or the like). The amount of modifications may vary depending on what modifications are made and perhaps even how the modified sequence performs. Other modifications may include: at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, and at least about 99%.

Epitope Mapping of the Mouse Anti-PAX8 [BC12] Binding Sequence:

In order to determine the peptide sequence of PAX8 that is recognized by [BC12], epitope mapping was conducted using two assays: direct ELISA and dot blot. In an ELISA assay, the sensitivity and specificity of the anti-PAX8 [BC12] antibody was determined by measuring the antibody titer at 1:500 and 1:1000. Overlapping peptides at a length of 15 amino acids each, covering the full length of the human PAX8 protein, were used to determine the preferred sequence of [BC12] binding. The anti-PAX8 [BC12] binds specifically to a peptide corresponding to residues 258-272 of PAX8, which is EQGLYPLPLLNSTLD identified as SEQ ID NO: 3. The result was further confirmed by dot blot assay.

For direct ELISA protocol, the plates were first coated with 100 µl of PAX8 peptides at 5 µg/mL in coating buffer (pH 9.5) overnight at 4° C., followed by blocking (3% BSA) at 200 µl/well for 1 hour at room temperature. The plates were incubated with purified PAX8 antibody at 100 ng/mL and 200 ng/mL separately for 1 hour at room temperature on an ELISA-plate shaker. Then the plates were washed five times with PBST (300 µl/well) followed by the addition of goat anti-mouse IgG-HRP to the plates and incubation for 1 hour on a plate-shaker. The plates were then washed with PBST (300 μl/well) and blotted to dry, and TMB was added at 100 μl/well, developed for 5 min on a shaker, followed by a stop solution (50 μl/well). Absorbance was measured at 450 nm on an ELISA plate reader according to the manufacturer's recommendation.

For the dot blot assay, a nitrocellulose membrane was blotted with 1 μl at a concentration of 1 mg/ml the peptide, quadruplicates per peptide. This membrane was incubated for 1 hour at room temperature until it was completely dry. The membrane was blocked with 3% BSA in TBST (50 mM Tris, 0.5 M NaCl, 0.05% Tween-20, pH 7.4) for 1 hour at room temperature, then mouse anti PAX8 antibody [BC12] was added at 200 ng/ml for 1 hr at RT in TBST. Then the membrane was washed for 3 times (10 minutes each) in TBST on an orbital shaker, followed by incubating with secondary antibody goat anti mouse IgG1-AP for 1 hour at room temperature in TBST. The membrane was washed 3 times (10 minutes each) in TBST on a rocker. The binding was detected by adding Western Glo Chemiluminescent detection reagents and exposing to film.

IHC Method with Anti-PAX8 BC12:

Immunohistochemistry using the mouse monoclonal PAX8 antibody [BC12] may be performed on formalin-fixed paraffin embedded (FFPE) tissue samples using procedures generally known to those in the art, as generally exemplified by the following non-limiting examples (washes with Tris-buffered saline, pH about 7.6, between steps):

1) Sections (~5 μm) of formalin fixed paraffin-embedded tissues may be mounted on commercially available microscope slides coated with polylysine.
2) Sections may be deparaffinized (using xylenes or a xylene-substitute) and may be rehydrated through a series of alcohol/water solutions, followed by blocking of endogenous peroxidases with about 3% hydrogen peroxide solution.
3) Samples may be subjected to heat-induced antigen retrieval using a citrate buffer in a pressure cooker (Reveal, Decloaking Chamber; Biocare Medical) and may be heated to about 125° C. for about 30 seconds. [Other antigen retrieval methods known to those skilled in the art (e.g., steamer, microwave oven, and enzyme) may also be acceptable.] Tissues may be allowed to cool for about 10 minutes and then may be rinsed with deionized water.
4) The PAX8 antibody [BC12] may be applied in a Tris-buffered solution (pH about 6.2) with bovine serum albumin as carrier protein for about 30 minutes.
5) Detection of the PAX8 antibody with a horseradish peroxidase (HRP) conjugated secondary antibody (MACH 4 Universal HRP-Polymer Detection, Biocare Medical) may be accomplished in two steps. An initial application of a rabbit anti-mouse IGg antibody for about 10 minutes may be followed by incubation with a goat anti-rabbit-HRP conjugate for about 10 minutes.
6) In a final detection step, 3,3'-diaminobenzidine (DAB) in buffer containing about 0.02% hydrogen peroxide (Betazoid DAB, Biocare Medical) may be applied. The oxidation of DAB through an HRP-mediated mechanism may result in precipitation of a brown, chromogenic product, perhaps allowing identification of sites of PAX8 expression.
7) Slides may be briefly counterstained in a modified Mayer's hematoxylin.

Results of IHC Staining with Mouse Monoclonal Anti-PAX8 Antibody [BC12]:

Using the above protocol, a variety of normal and neoplastic tissues were evaluated for PAX8 expression using BC12 and compared to staining patterns using a rabbit polyclonal anti-PAX8 antibody (10336-1-AP, Proteintech). The mouse and rabbit PAX8 antibodies exhibited similar sensitivities for a variety of normal and neoplastic tissues. FIGS. 1-5 show several examples of the PAX8 staining on normal and tumor tissues for kidney and ovarian examples.

The monoclonal mouse PAX8 antibody may offer distinct advantages with its improved specificity and even particularly its lack of cross-reactivity with lymphocytes, pancreatic tissue (islets of Langerhans), and neuroendocrine cells of the stomach. FIGS. 6, 7, 8, and 9 show comparisons of the mouse monoclonal antibody [BC12] with the rabbit polyclonal antibody, demonstrating the similarities in positive staining for PAX8 by both antibodies, but the greater specificity of BC12, which may not stain B-cells, as compared to the rabbit monoclonal antibody, where B-cell staining may be observed.

Figure 14:
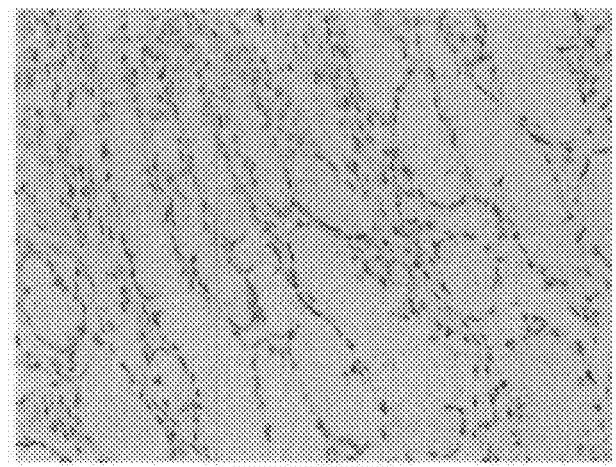
FIG. 14 shows an example of PAX8 staining using PAX8 Mouse Monoclonal [BC12] on stomach tissue at 20× wherein no stain is present.
Figure 15:
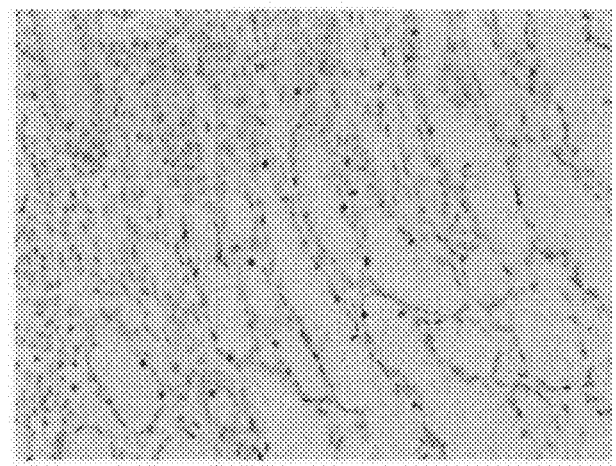
FIG. 15 shows an example of PAX8 staining using PAX8 Rabbit Polyclonal on stomach tissue at 20× wherein stain is present. Note: A chromogranin IHC stain confirmed that the rabbit PAX8 staining was of neuroendocrine origin.

Additionally, the mouse monoclonal PAX8 antibody [BC12] may have an advantage of specificity versus pancreatic tissue and certain neuroendocrine tumors such as carcinoids; whereas the rabbit polyclonal antibody may stain normal and neoplastic pancreatic tissues, and may also stain certain carcinoids. BC12 may not stain pancreatic tissue as may be understood in FIGS. 10, 11, 12, and 13. Furthermore BC12 has demonstrated increased specificity on stomach tissue as well. The rabbit polyclonal PAX8 antibody may stain a subset of cells in stomach tissue that may not be stained by BC12 as can be understood in FIGS. 14 and 15. Cells stained in FIG. 15 stained positive by a chromogranin IHC assay; and thus, confirmed as neuroendocrine origin.

In some embodiments of the present invention, the mouse monoclonal PAX8 antibody [BC12] may be suitable for use in many variations of the above protocols and other methods known to those in the art. Specimens stained with BC12 may be archived using a permanent mounting media and a coverslip. The antibody [BC12] may also be used in an automated staining instrument, using standard protocols. One can also envision the use of many alternative detection methods (e.g., fluorescence), detection enzymes (e.g., alkaline phosphatase (AP), beta-galactosidase), and perhaps even chromogens (e.g., 3-amino-9-ethylcarbazole, 5-bromo-4-chloro-3-indolyl phosphate, 3,3',5,5'-tetramethylbenzidine, 5-bromo-4-chloro-3-indolyl-β-D-glucuronide), generally known to those in the art.

The epitope for BC12 was shown to be included in the residues 258-272 of PAX8, which is EQGLYPLPLLNSTLD identified as SEQ ID NO: 3. The epitope of the mouse monoclonal PAX8 antibody, or a portion thereof, may be a useful antigen for the production of new monoclonal antibodies, including production in species other than mouse (e.g. rabbit, goat, horse, chicken, etc.).

While the use of BC12 in immunohistochemistry of formalin-fixed paraffin embedded tissues is described here, its utility in other immunoassays may be readily envisioned and are meant to be included in this application. In particular, it may be well known that many of the same reagents used in IHC of FFPE may also be used in IHC of frozen-tissue sections. BC12 may also be useful in other immunoassays, including ELISA, perhaps using generally known methods.

In another aspect of the invention, perhaps related to IHC, a PAX8 antibody may be used in conjunction with one or more additional primary antibodies as part of a cocktail, to perform a "double-stain" procedure (also described as multistain or even multiplex). Such "double-stain" procedures may be generally well known in the art; however, the best combinations of primary antibodies for a particular diagnostic application may not be known.

In this method, a mouse monoclonal PAX8 antibody [BC12] could be combined with one or more antibodies in a single primary antibody cocktail. At least one of the additional antibodies could be derived from a species perhaps even other than mouse such as a rabbit antibody. Species may include but is not limited to mouse, rabbit, goat, horse, chicken, human, any combinations thereof, or the like. In this manner, the multiple antibodies in the primary antibody cocktail may be differentiated in the subsequent detection and even visualization steps. For example, following incubation of the tissue sample with the primary antibody cocktail, a cocktail of goat anti-mouse antibody conjugated to HRP and a goat anti-rabbit antibody conjugated to AP may be applied. Subsequently, chromogens specific for HRP and AP may be sequentially applied. In this manner, two or more targets may be identified on the same tissue sample with the resulting two colors. In this specific example, mouse primary antibodies (including BC12) could result in brown (DAB) staining and rabbit primary antibodies could result in red (Fast Red) staining. Multiplex IHC may also employ primary antibodies from the same host species, resulting the staining of the same color; however, the antibodies may be distinguished by different cellular localization patterns (cytoplasmic, membrane or nuclear).

Specifically, multiplex IHC may be performed by preparing FFPE tissues for staining in the usual manner, including dewaxing, hydration, and antigen retrieval. A cocktail of primary antibodies (in a buffered diluent with carrier protein [e.g. BSA] and preservative [e.g. sodium azide]) is applied to the tissue sample for a period of typically 30 minutes. Importantly, the primary antibodies in the cocktail are isolated from two different host-species (e.g. mouse and rabbit). For example, a primary antibody cocktail containing mouse anti-p63 and rabbit anti-P504S is commonly used in prostate diagnosis. Secondary antibodies conjugated to enzyme for detection (e.g. alkaline phosphatase [AP], horseradish peroxidase [HRP]) may then be applied to the tissue sample, typically for a period of 30 minutes. These secondary antibody conjugates are typically raised in goat and bind the mouse or rabbit IgG of the primary antibodies previously applied. For example, a cocktail of goat anti-mouse-HRP and goat anti-rabbit-AP is often applied to the mouse anti-p63 and rabbit anti-P504S described above. In this example, p63 (a mouse antibody) would be bound by goat anti-mouse-HRP and P504S (a rabbit antibody) would be bound by goat anti-rabbit-AP. The presence and localization of both antibodies may then be distinguished by the sequential application of chromogens resulting in different colors. Specifically, each of the applied chromogens reacts with only one of the two detection enzymes (AP or HRP) to produce a colored stain at the site of the antibody complex. In the p63+P504S example, 3,3'-diaminobenzidine (DAB) may produce a brown stain, catalyzed by the HRP of the p63 antibody complex, while Fast Red (a diazonium salt and naphthol phosphate) may produce a red stain, catalyzed by the AP of the P504S antibody complex.

Multiplex IHC has several advantages over traditional single-stain methods. For example, doubles-staining may take less time and use less reagents than a single-stain method. The opportunity to visualize perhaps by color results of two or more antigens in the same tissue section may greatly ease the pathologist's interpretation. Double-staining also has the advantage of consuming less of a tissue sample (i.e. a single section), thus conserving precious tissue for other tests.

Multiple alternatives to a double-staining method are possible, including but not limited to the use of more than two antibodies, the use of species other than mouse and rabbit, other chromogens and detection systems, a different order of detection steps, the sequential application of antibody regents instead of the use of cocktails, the use of goat anti-mouse-AP and goat anti-rabbit-HRP secondary antibodies, and perhaps even modifications resulting in three or more colors (which may require a denaturing step).

An anti-PAX8 antibody, such as, but not limited to BC12, may be used in the primary antibody cocktail of double-stain procedures in an method that may be useful for clinical diagnosis. For example, in cases where a tumor of unknown origin is being investigated, or a differential diagnosis between a kidney cancer and another cancer is being considered, the combination of PAX8 with another antibody may aid in the diagnosis.

An antibody cocktail may include a composition with at least two antibodies or fragments thereof where at least one antibody binds specifically to PAX8 and at least one other antibody binds to an antigen including but not limited to: GATA-3, p63, PSA, ER, Mammaglobin, GCDFP-15, NKX3.1, Napsin A, TTF-1, CK20, CDX2, ERG, or the like, and any combination thereof. Compositions may include combination such as but not limited to PAX8 and GATA-3; PAX8 and p63; PAX8 and PSA; PAX8 and PSA and GATA-3; PAX8 and ER and Mammoglobin and GCDFP-15; PAX8 and ER; PAX8 and Mammoglobin; PAX8 and GCDFP-15; PAX8 and NKX3.1; PAX8 and Napsin A and TTF-1; PAX8 and Napsin A; PAX8 and TTF-1; PAX8 and CD20 and CDX2; PAX8 and CD20; PAX8 and CDX2; PAX8 and ERG and GATA-3; PAX8 and ERG; or the like, or any combination thereof. The antibody cocktail may include any antibody which specifically binds to PAX8; may be an antibody which specifically binds to PAX8 but not to B-cells; may be the BC12 antibody or portions thereof, fragments thereof, or the like; may be an antibody which specifically binds to PAX8 but not to neuroendocrine cells, pancreatic cells, or any combination thereof; or the like.

Methods for antibody cocktails may include detecting at least two different proteins in a biological sample, comprising the steps of contacting a biological sample (2) with a composition comprising at least two antibodies or fragments thereof, wherein at least one of said at least two antibodies or fragments thereof binds specifically to at least PAX8, to form an antigen-antibody complex (3); and perhaps even detecting said antigen-antibody complex.

Antibodies that may be useful for diagnosis when combined with a mouse monoclonal PAX8 antibody [BC12] in a primary antibody cocktail for use in multi-stain procedures may include:

| Antibody Cocktail | Diagnosis of tumor of unknown origin or differential diagnosis |
| --- | --- |
| PAX8 + GATA-3 | Renal vs Bladder or Breast |
| PAX8 + p63 | Renal vs Renal Pelvis |
| PAX8 + PSA + GATA-3 | Renal vs Prostate vs Bladder |
| PAX8 + ER and/or Mammaglobin and/or GCDFP-15 | Renal vs Breast |
| PAX8 + NKX3.1 | Renal vs Prostate |
| PAX8 + Napsin A and/or TTF-1 | Renal vs. Lung |
| PAX8 + CK20 and/orCDX2 | Renal vs. Colon |
| PAX8 + ERG + GATA-3 | Renal vs Prostate vs Bladder |

Examples of antibody cocktails containing PAX8 are described below. In some cases, example cocktails were stained on normal tissues where the antigen is known to be present in both normal and neoplastic tissues.

PAX8+GATA-3:

A double-stain IHC primary antibody cocktail containing mouse monoclonal PAX8+rabbit monoclonal GATA-3 may be useful for diagnosis, including for the discrimination of renal carcinomas (PAX8) from breast or urothelial carcinomas (GATA-3).

PAX8+p63:

p53 homologue p63 encodes for different isotypes able to either transactivate p53 reporter genes (TAp63) or act as p53-dominant-negatives. p63 is detected in prostatic basal cells in normal prostate, however, it is negative in malignant tumors of the prostate gland. Thus, p63 is a useful differential marker for benign and malignant tumors of the prostate gland. p63 is also a marker of myoepithelial cells in breast ducts and may be useful in identifying breast carcinoma. As a marker or urothelial carcinoma, p63 may also stain renal pelvis urothelial carcinoma. A double-stain of PAX8+p63 may be useful in the differential diagnosis of carcinoma of the renal pelvis from renal cell carcinoma.

Figure 16:
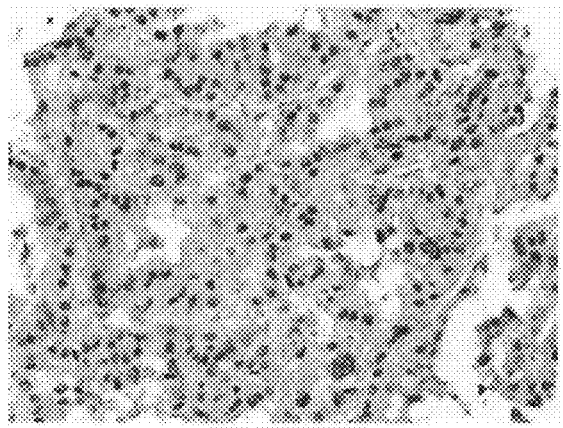
FIG. 16 shows an example of staining of using PAX8+p63 antibody cocktail on renal cell carcinoma.
Figure 17:
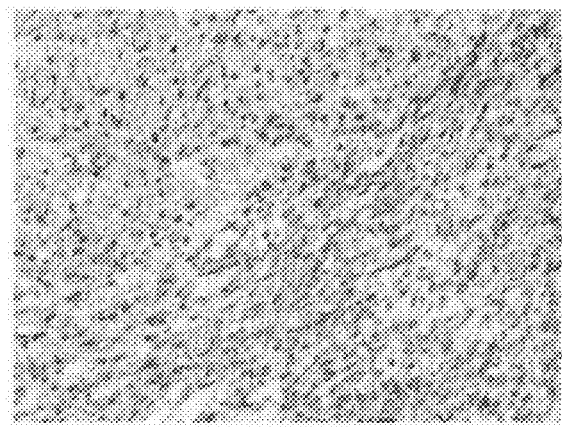
FIG. 17 shows an example of staining of using PAX8+p63 antibody cocktail on normal bladder.

FIGS. 16 and 17 show an example of multiplex IHC staining of mouse monoclonal PAX8 [BC12]+rabbit monoclonal p63 [EPR5701] (Cell Signaling) on renal cell carcinoma (FIG. 16) and normal bladder (FIG. 17). A detection system of goat anti-mouse-HRP+goat anti-rabbit-AP with DAB and Fast Red chromogens, resulting in brown (PAX8) or red (p63) staining.

PAX8+PSA+GATA-3:

PSA is a chymotrypsin-like serine protease produced by the prostate epithelium. PSA is used to confirm prostatic acinar cell origin in primary and metastatic carcinomas and to rule out non-prostatic carcinoma mimics. A triple-stain of PAX8+PSA+GATA-3 may be useful in the differential diagnosis of renal cell carcinoma, prostate adenocarcinoma and urothelial carcinoma.

GATA-3 (GATA binding protein 3) is a member of the GATA family of transcription factors. Among several other roles, GATA-3 has is as a key player in luminal cell differentiation in the mammary gland. The expression of GATA-3 has a strong association with the expression of estrogen receptor-alpha (ER) in breast cancer, and there is mounting evidence that GATA-3 can be used as a clinical marker to determine response to hormonal therapy and to refine the prognosis of breast cancer patients. GATA-3 has also been shown to be a novel marker for bladder cancer. In one study, GATA-3 stained 67% of 308 urothelial carcinomas, but none for prostate or renal carcinomas. A double-stain of PAX8+PSA+GATA-3 may be useful in the differential diagnosis of renal cell carcinoma, prostate adenocarcinoma and urothelial carcinoma, see FIGS. 18, 19, and 20.

Figure 18:
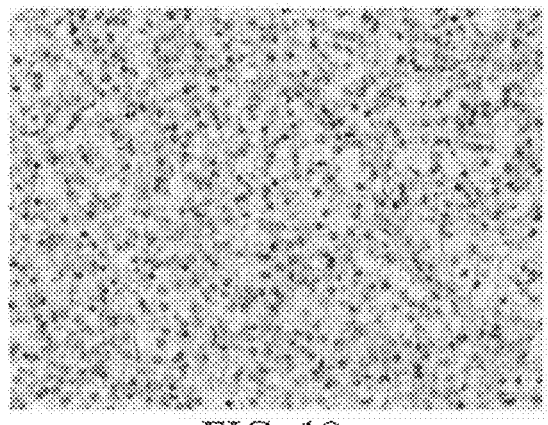
FIG. 18 shows an example of staining of using PAX8+PSA+GATA-3 antibody cocktail on renal cell carcinoma.
Figure 19:
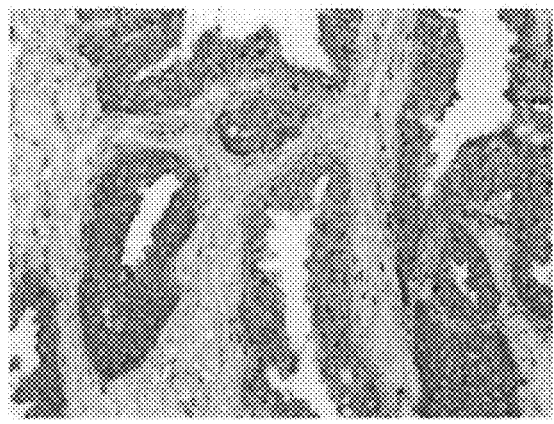
FIG. 19 shows an example of staining of using PAX8+PSA+GATA-3 antibody cocktail on prostate adenocarcinoma.
Figure 20:
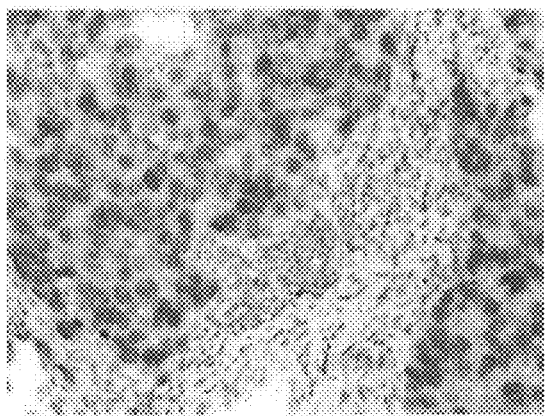
FIG. 20 shows an example of staining of using PAX8+PSA+GATA-3 antibody cocktail on urothelial carcinoma.

FIGS. 18, 19, and 20 show an example of multiplex IHC staining of mouse monoclonal PAX8 [BC12]+rabbit monoclonal PSA [EP1588Y] (e.g., Biocare Medical)+rabbit monoclonal GATA-3 [D13C9] (Cell Signaling) on renal cell carcinoma (FIG. 18), prostate adenocarcinoma (FIG. 19) and urothelial carcinoma (FIG. 20). A detection system of goat anti-mouse-HRP+goat anti-rabbit-AP with DAB and Fast Red chromogens, resulting in nuclear brown (PAX8), cytoplasmic red (PSA) or nuclear red (GATA-3) staining.

Figure 21:
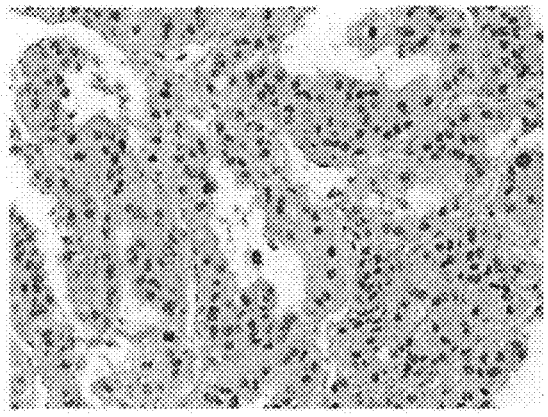
FIG. 21 shows an example of staining of using PAX8+ER+mammaglobin cocktail on renal cell carcinoma.
Figure 22:
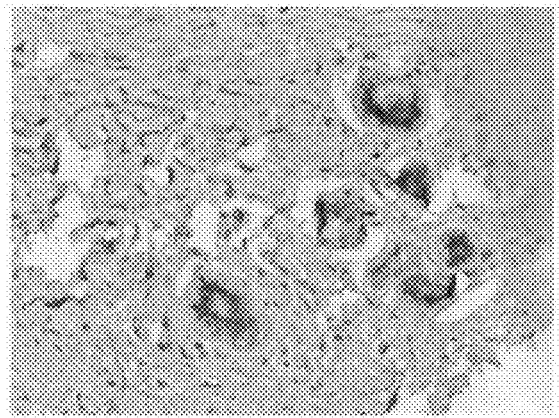
FIG. 22 shows an example of staining of using PAX8+ER+mammaglobin cocktail on normal breast.

PAX8+ER+Mammaglobin:

Estrogen receptor alpha (ER) is a nuclear transcription factor and a member of the steroid hormone receptor family. ER is routinely used in the diagnosis, prognosis and prediction of response to hormonal therapy for breast cancer patients. Mammaglobin is a mammary-specific member of the uteroglobin family and is known to be overexpressed in human breast cancer. In normal breast tissue, mammaglobin labels breast ductal and lobular epithelial cells. However, mammaglobin is expressed in a higher percentage of lobular carcinoma versus ductal cell carcnimoma. A double-stain or perhaps even a triple-stain of PAX8+ER+mammaglobin may be useful in the diganosis of renal cell carcinoma versus breast carcinoma. FIGS. 21 and 22 show staining of the PAX8+ER+mammaglobin cocktail.

FIGS. 21 and 22 show multiplex IHC staining of a mouse monoclonal PAX8 [BC12]+rabbit monoclonal ER [SP1] (Biocare Medical)+rabbit monoclonal Mammaglobin [31-A5] (Zeta) on renal cell carcinoma (FIG. 21) and normal breast (FIG. 22). A detection system of goat anti-mouse-HRP+goat anti-rabbit-AP with DAB and Fast Red chromogens, resulting in nuclear brown (PAX8), cytoplasmic red (Mammaglobin) or nuclear red (ER) staining.

PAX8+NKX3.1:

The homeodomain containing transcription factor NKX3.1 is a putative prostate tumor suppressor that is expressed in a largely prostate-specific and androgen-regulated manner. NKX3.1 protein has been found to be positive in the vast majority of primary pro static adenocarcinomas. The sensitivity for identifying metastatic prostatic adenocarcinomas overall was 98.6% (68/69 cases positive) for NKX3.1. NKX3.1 stains nuclei in both normal and prostate cancer. A double-stain of PAX8+NKX3.1 may be useful in the differential diagnosis of renal cell carcinoma from prostate adenocarcinoma, see FIGS. 23 and 24.

Figure 23:
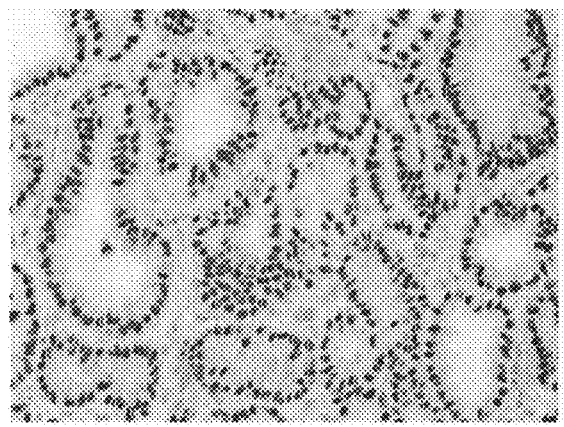
FIG. 23 shows an example of staining of using PAX8+NKX3.1 antibody cocktail on renal cell carcinoma.
Figure 24:
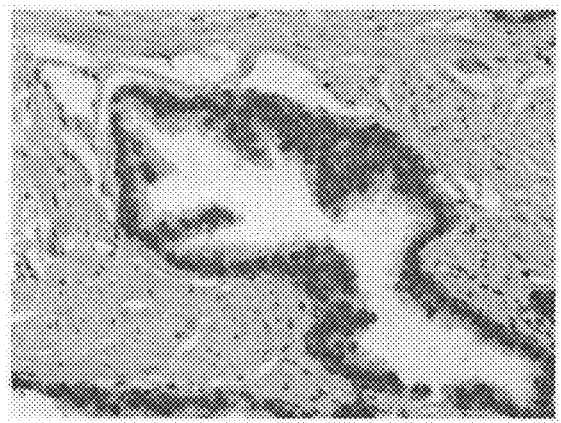
FIG. 24 shows an example of staining of using PAX8+NKX3.1 antibody cocktail on prostate adenocarcinoma.

FIGS. 23 and 24 show multiplex IHC staining of mouse monoclonal PAX8 [BC12]+rabbit polyclonal NKX3.1 (e.g., Biocare Medical, CP422) on renal cell carcinoma (FIG. 23) and prostate adenocarcinoma (FIG. 24). A detection system of goat anti-mouse-HRP+goat anti-rabbit-AP with DAB and Fast Red chromogens, resulting in brown (PAX8) or red (NKX3.1) staining.

Figure 25:
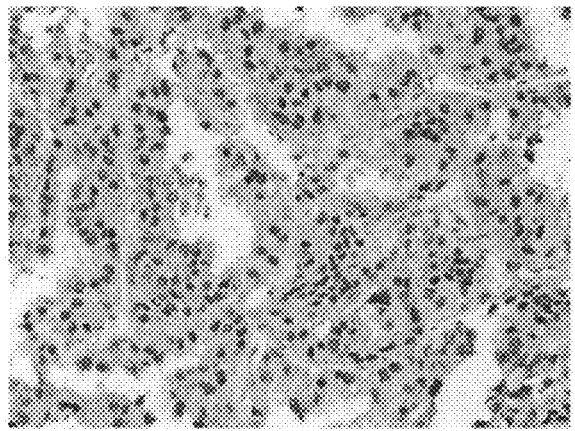
FIG. 25 shows an example of staining of using PAX8+Napsin A antibody cocktail on renal cell carcinoma.

PAX8+Napsin A:

Napsin A is an aspartic detected in the cytoplasm of type 2 pneumocytes and alveolar macrophages. Napsin A is a sensitive and specific marker for lung adenocarcinomas. In one study, Napsin A identified 70 of 83 (84%) lung adenocarcinomas. A double-stain of PAX8+Napsin A may be useful in the differential diagnosis of renal cell carcinoma from lung adenocarcinoma. FIGS. 25 and 25 show staining of a PAX8+Napsin A antibody cocktail.

Figure 26:
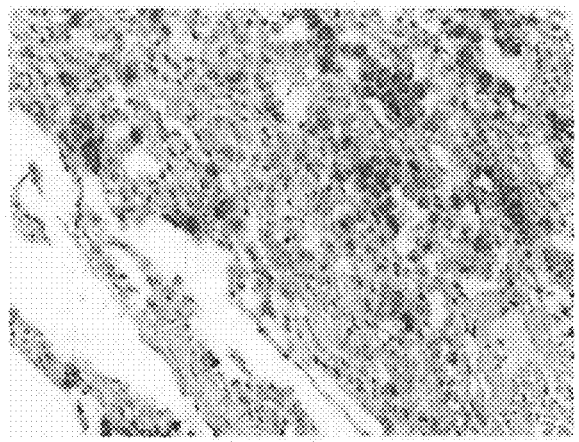
FIG. 26 shows an example of staining of using PAX8+Napsin A antibody cocktail on normal lung.

FIGS. 25 and 26 show multiplex IHC staining of mouse monoclonal PAX8 [BC12]+rabbit polyclonal Napsin A (Biocare Medical, PP434) on renal cell carcinoma (FIG. 25) and normal lung (FIG. 26). A detection system of goat anti-mouse-HRP+goat anti-rabbit-AP with DAB and Fast Red chromogens, resulting in brown (PAX8) or red (Napsin A) staining.

Figure 27:
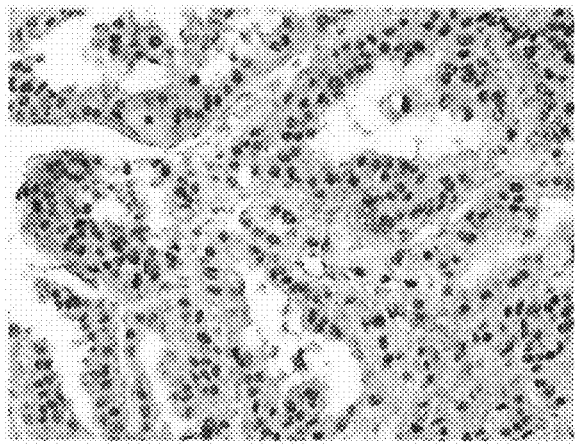
FIG. 27 shows an example of staining of using PAX8+CK20 antibody cocktail on renal cell carcinoma.
Figure 28:
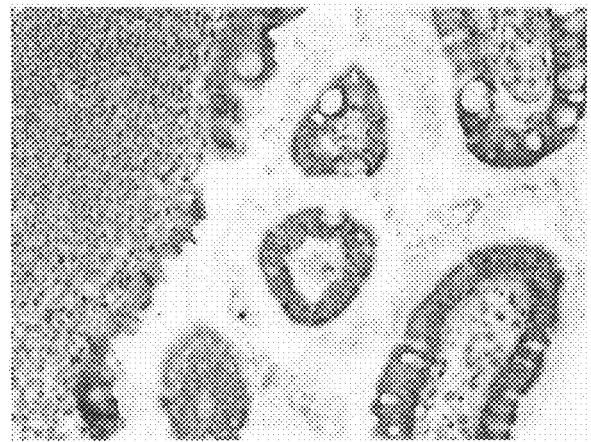
FIG. 28 shows an example of staining of using PAX8+CK20 antibody cocktail on normal colon.

PAX8+CK20:

Cytokeratin 20 (CK20) is a 46 kDa intermediate filament protein that is a useful marker in the identification of colon adenocarcinoma. A double-stain of PAX8+CK20 may be useful in the differential diagnosis of renal cell carcinoma from colon adenocarcinoma. FIGS. 27 and 28 show staining of a PAX8+CK20 antibody cocktail.

FIGS. 27 and 28 show multiplex IHC staining of mouse monoclonal PAX8 [BC12]+rabbit monoclonal CK20 [EP23] (Epitomics) on renal cell carcinoma (FIG. 27) and normal colon (FIG. 28). A detection system of goat anti-mouse-HRP+goat anti-rabbit-AP with DAB and Fast Red chromogens, resulting in brown (PAX8) or red (CK20) staining.

PAX8+ERG+GATA-3:

In human prostate cancer, the ERG oncogene is frequently overexpressed due to chromosomal translocations involving ERG and regulatory sequences of the TMPRSS2 or other androgen responsive genes. Strong concordance between the TMPRSS2-ERG translocation and detection of the protein product by IHC has been demonstrated. Anti-ERG antibodies are specific markers for prostate adenocarcinoma. A double-stain of PAX8+ERG may be useful in the differential diagnosis of renal cell carcinoma from prostatic adenocarcinoma. A double-stain of PAX8+ERG+GATA-3 may be useful in the differential diagnosis of renal cell carcinoma from prostatic adenocarcinoma and urothelial carcinoma, see FIGS. 29, 30, and 31.

Figure 29:
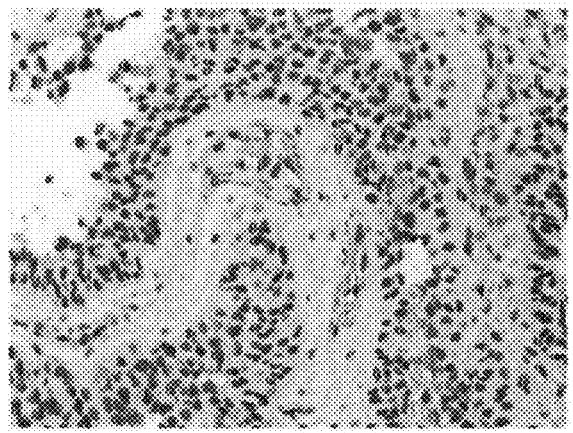
FIG. 29 shows an example of staining of using PAX8+ERG+GATA-3 antibody cocktail on renal cell carcinoma.
Figure 30:
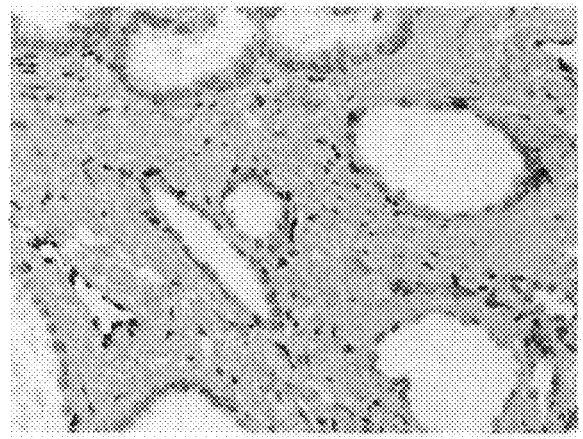
FIG. 30 shows an example of staining of using PAX8+ERG+GATA-3 antibody cocktail on prostatic adenocarcinoma.
Figure 31:
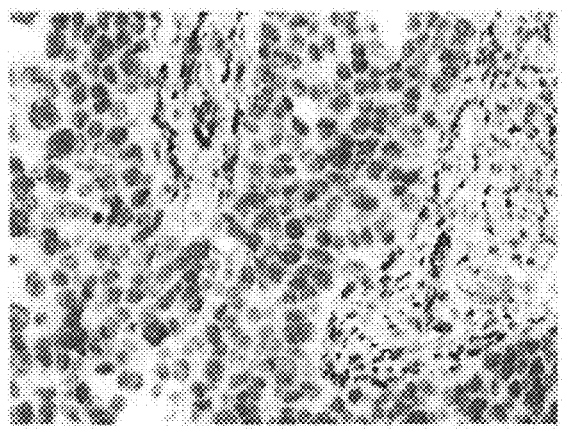
FIG. 31 shows an example of staining of using PAX8+ERG+GATA-3 antibody cocktail on urothelial carcinoma.

FIGS. 29, 30, and 31 show multiplex IHC staining of mouse monoclonal PAX8 [BC12]+rabbit monoclonal ERG [ER3863] (Epitomics)+rabbit monoclonal GATA-3 [D13C9] (Cell Signaling) on renal cell carcinoma (FIG. 29), prostatic adenocarcinoma (FIG. 30) and urothelial carcinoma (FIG. 31). A detection system of goat anti-mouse-HRP+goat anti-rabbit-AP with DAB and Fast Red chromogens, resulting in brown (PAX8), or red (ERG or GATA-3) staining. ERG and GATA-3 staining may be distinguished by morphology. (Note that normal endothelial cells present in most tissues are known to stain with ERG.)

The mouse monoclonal PAX8 antibody [BC12] may be specific for detection of PAX8 and may be useful in immunohistochemical procedures for diagnosis of several types of cancers in human tissue samples. In particular, BC12, nucleic acid sequences SEQ ID NO: 1 and/or SEQ ID NO: 2, and amino acid SEQ ID NO: 3 can be used and have advantages over previously known PAX8 antibodies, including greater specificity versus B-cells, as well as a lack of cross-reactivity and staining of pancreatic tissues and neuroendocrine cells of the stomach.

As can be easily understood from the foregoing, the basic concepts of the present invention may be embodied in a variety of ways. It involves both antibody techniques as well as devices to accomplish the appropriate antibody. In this application, the antibody techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "detection" or "detector" should be understood to encompass disclosure of the act of "detecting"—whether explicitly discussed or not—and, conversely, were there effectively disclosure of the act of "detecting", such a disclosure should be understood to encompass disclosure of a "detector" and even a "means for detecting." Such changes and alternative terms are to be understood to be explicitly included in the description. Further, each such means (whether explicitly so described or not) should be understood as encompassing all elements that can perform the given function, and all descriptions of elements that perform a described function should be understood as a non-limiting example of means for performing that function.

Any law, statutes, regulations, or rules mentioned in this application for patent; or patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed below or in any list of References or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

| U.S. Pat. No. | Kind | Date of Patent | Inventor |
|---|---|---|---|
| 6,051,693 |  | 2000 Apr. 18 | Handley et al. |
| 7,422,739 | B2 | 2008 Sep. 09 | Anderson et al. |
| 7,785,803 | B2 | 2010 Aug. 31 | Achen et al. |
| 7,875,705 | B2 | 2011 Jan. 25 | Iwanari et al. |
| 7,935,794 | B2 | 2011 May 03 | Pullen |
| 7,935,795 | B2 | 2011 May 03 | Nakajima |
| 7,935,796 | B2 | 2011 May 03 | Lee et al. |
| 7,973,138 | B2 | 2011 Aug. 05 | Liang et al. |
| 8,153,126 | B2 | 2012 Apr. 10 | Violette et al. |

| Publication No. | Kind | Pub Date | Assignee |
|---|---|---|---|
| 20050186642 | A1 | 2005 Aug. 25 | Tacha |
| 20100004782 | A1 | 2010 Feb. 25 | Tacha |
| 20100047825 | A1 | 2010 Feb. 25 | Biocare Medical, Inc. |

| Foreign Patents | Country Code | Kind | Pub. Date | Patentee/Applicant |
|---|---|---|---|---|
| 2005083802 | WO | A1 | 2005 Sep. 09 | Biocare Medical, LLC |

Nonpatent Literature

Albadine, R., Schultz, L., Illei, P., Ertoy, D., Hicks, J., Sharma, R., Epstein, J., Netto, G.; *PAX8(+)/p63(−) Immunostaining Pattern in Renal Collecting Duct Carcinoma (CDC), A Useful Immunoprofile in the Differential Diagnosis of CDC Versus Urothelial Carcinoma of Upper Unirary Tract*; Am/Surg Pathol, Vol. 34, No. 7, July 2010, pp 965-969.
Avery, A. K. et al. *Use of antibodies to RCC and CD10 in the differential diagnosis of renal neoplasms.* Am J Surg Pathol. 2000 February; 24(2): 203-10
Bowen, N. J. et al. *Emerging roles for PAX8 in ovarian cancer and endosalpingeal development.* Gynecol Oncol. 2007, February; 104(2): 331-7
Buchwalow, I. et al. *Immunohistochemistry: Basics and Methods.* Springer Press. 1st ed. 2010
Carson, F. L. et al. *Histotechnology: A Self-Instructional Text.* American Society for Clinical Pathology; 3rd ed. 2009
Geramizadeh, B. et al. *Useful markers for differential diagnosis of oncocytoma, chromophobe renal cell carcinoma and conventional renal cell carcinoma*, Indian J Pathol Microbiol. 2008 April-June; 51(2): 167-71
Haynes, C., Sangoi, A., Pai, R.; *PAX8Is Expressed in Pancreatic Well-Differentiated Neuroendocrine Tumors and in Extrapancreatic Poorly Differentiated Neuroendocrine Carcinomas in Fine-Needle Aspiration Biopsy Specimens*; Cancer Cytopathology, Jun. 25, 2011, pp 193-201.
Köbel, M. et al. *Ovarian carcinoma subtypes are different diseases: implications for biomarker studies.* PLoS Med. 2008, Dec. 2; 5(12): e232
Koelma, I. A. et al. *The value of tumours marker CA 125 in surgical pathology*, Histopathology. 1987 March; 11(3): 287-94
Kuehn, A. et al. *Expression analysis of kidney-specific cadherin in a wide spectrum of traditional and newly recognized renal epithelial neoplasms: diagnostic and histogenetic implications.* Am J Surg Pathol. 2007 October; 31(10): 1528-33
Laury, A., Hornick, J., Perets, R., Krane, J., Corson, J., Drapkin, R., Hirsch, M.; *PAX8 Reliably Distinguishes Ovarian Serous Tumors from Malignant Mesothelioma*; Am/Surg Pathol, Vol. 34, No. 5, May 2010, pp 627-635.
Laury, A., Perets, R., Piao, H., Krane, J., Barletta, J., French, C., Chirieac, L., Lis, R., Loda, M., Hornick, J., Drapkin, R., Hirsch, M.; *A Comprehensive Analysis of PAX8 Expression in Human Epithelial Tumors*; Am/Surg Pathol, Vol. 35, No. 6, June 2011, pp 816-826
Leake, J. et al. *Immunocytochemical and serological expression of CA 125: a clinicopathological study of 40 malignant ovarian epithelial tumours.* Histopathology. 1994 January; 24(1): 57-64
Lee, A. H. et al. *The expression of Wilms' tumour-1 and CA125 in invasive micropapillary carcinoma of the breast.* Histopathology. 2007 December; 51(6): 824-8
Long, K., Srivastava, A., Hirsch, M., Hornick, J.; *PAX8 Expression in Well-differentiated Pancreatic Endocrine Tumors: Correlation With Clinicopathologic Features and Comparison With Gastrointestinal and Pulmonary Carcinoid Tumors*; Am/Surg Pathol, Vol. 34, No. 5., May 2010; pp 723-729.
Lorenzo, P., Moreno, C., Delgado, I., Cobo-Vuilleumier, N., Meier, R., Gomez-Izquierdo, L., Berney, T., Garcia-Carbonero, R., Rojas, A., Gauthier, B.; *Immunohistochemical assessment of Pax8 expression during pancreatic islet development and in human neuroendocrine tumors*; Histochem Cell Biol (2011) 136: 595-607.
Mazal, P. R. et al. *Expression of kidney-specific cadherin distinguishes chromophobe renal cell carcinoma from renal oncocytoma.* Hum Pathol. 2005 January; 36(1): 22-8
Mazal, P. R. et al. *Expression of aquaporins and PAX-2 compared to CD10 and cytokeratin 7 in renal neoplasms: a tissue microarray study.* Mod Pathol. 2005 April; 18(4): 535-40.

Moretti, L., Medeiros, L., Kunkalla, K., Williams, M., Singh, R., Vega, F.;*N-terminal PAX8 polyclonal antibody shows cross-reactivity with N-terminal region of PAX5 and is responsible for reports of PAX8 positivity in malignant lymphomas*; Modern Pathology (2011), 1-6.

Nonaka, D. et al. *Diagnostic utility of thyroid transcription factors Pax8 and TTF-2 (FoxE1) in thyroid epithelial neoplasms.* Mod Pathol. 2008 February; 21(2): 192-2004

Nonaka, D. et al. *Expression of pax8 as a useful marker in distinguishing ovarian carcinomas from mammary carcinomas.* Am J Surg Pathol. 2008 October; 32(10): 1566-71

Ozcan, A., Shen, S., Hamilton, C., Anjana, K., Coffey, D., Krishnan, B., Truong, L.; *PAX8 expression in non-neoplastic tissues, primary tumors, and metastatic tumors: a comprehensive immunohistochemical study.*; Modern Pathology (2011) 24, 751-764.

Reid-Nicholson, M. et al. *Immunophenotypic diversity of endometrial adenocarcinomas: implications for differential diagnosis.* Mod Pathol. 2006 August; 19(8): 1091-100

Sangoi, A., Ohgami, R., Pai, R., Beck, A., McKenney, J., Pai, R.; *PAX8 expression reliably distinguishes pancreatic well-differentiated neuroendocrine tumors and pancreatic acinar cell carcinoma*; Modern Pathology (2011) 24, 412-424.

Sosa-Pineda, B. *The gene Pax4 is an essential regulator of pancreatic beta-cell development.* Mol Cells. 2004 Dec. 31; 18(3): 289-94

Tacha, D., Zhou, D., Cheng, L.; *Expression of PAX8 in Normal and Neoplastic Tissues-A Comprehensive Immunohistochemical Study*; Appl Immunohistochem Mol Morphol, Vol. 19, No. 4, July 2011, pp 293-299.

Thus, the applicant(s) should be understood to have support to claim and make a statement of invention to at least: i) each of the antibody devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) an apparatus for performing the methods described herein comprising means for performing the steps, xii) the various combinations and permutations of each of the elements disclosed, xiii) each potentially dependent claim or concept as a dependency on each and every one of the independent claims or concepts presented, and xiv) all inventions described herein.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC,* 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. An antibody or fragment thereof that specifically binds to the amino acid sequence consisting of SEQ ID NO: 3.

2. An antibody or fragment thereof according to claim 1 wherein said antibody or fragment thereof comprises a polypeptide of the amino acid sequence encoded by the nucleic acid sequence of SEQ ID NO: 1 and SEQ ID NO: 2.

3. An antibody or fragment thereof according to claim 1 wherein said antibody or said fragment thereof comprises a light chain variable region comprising the amino acid sequence encoded by the nucleic acid sequence of SEQ ID NO: 2 and a heavy chain variable region comprising the amino acid sequence encoded by the nucleic acid sequence of SEQ ID NO: 1.

4. An antibody or fragment thereof according to claim 1 wherein said antibody or said fragment thereof binds specifically to at least PAX8.

5. An antibody or fragment thereof according to claim 4 wherein said antibody or said fragment thereof which binds specifically to at least PAX8 comprises an antibody or fragment thereof which binds specifically to at least PAX8 and does not bind to B-cells.

6. An antibody or fragment thereof according to claim 4 wherein said antibody or said fragment thereof which binds specifically to at least PAX8 comprises an antibody or fragment thereof which binds specifically to at least PAX8 and does not specifically bind to cells selected from a group consisting of neuroendocrine cells, pancreatic cells, and any combination thereof.

7. A composition according to claim 1 comprising said antibody or fragment thereof that specifically binds to at least one polypeptide with an amino acid sequence comprising residues of SEQ ID NO: 3 and at least one other antibody or fragment thereof.

8. A composition according to claim 7 wherein said at least two antibodies or fragments thereof are obtained from at least two different species.

9. A composition according to claim 8 wherein said at least two different species is selected from a group consisting of mouse, rabbit, goat, horse, chicken, human, and any combination thereof.

10. A composition according to claim 7 wherein said at least two antibodies or fragments thereof are used in a double-stain procedure.

11. A composition according to claim 7 wherein said at least two antibodies or fragments thereof are used in a staining procedure capable of providing different visualization results.

12. A composition according to claim 11 wherein said visualization results comprise color results.

13. A composition according to claim 7 wherein said at least one other antibody or fragment thereof binds specifically to an antigen selected from a group consisting of GATA-3, p63, PSA, ER, Mammaglobin, GCDFP-15, NKX3.1, Napsin A, TTF-1, CK20, CDX2, ERG, and any combination thereof.

14. A composition according to claim 7 wherein at least two antibodies or fragments thereof each bind specifically to proteins selected from a group consisting of:
PAX8 and GATA-3;
PAX8 and p63;
PAX8 and PSA;
PAX8 and PSA and GATA-3;
PAX8 and ER and Mammoglobin and GCDFP-15;
PAX8 and ER;
PAX8 and Mammoglobin;
PAX8 and GCDFP-15;
PAX8 and NKX3.1;
PAX8 and Napsin A and TTF-1;
PAX8 and Napsin A;
PAX8 and TTF-1;
PAX8 and CD20 and CDX2;
PAX8 and CD20;
PAX8 and CDX2;
PAX8 and ERG and GATA-3; and
PAX8 and ERG.

15. An antibody according to claim 1 wherein said antibody comprises a monoclonal antibody.

16. An antibody according to claim 15 wherein said monoclonal antibody is selected from a group consisting of a mouse monoclonal antibody, a rabbit monoclonal antibody, a goat monoclonal antibody, a horse monoclonal antibody, a chicken monoclonal antibody, a humanized monoclonal antibody, a chimeric antibody, and any combination thereof.

17. An antibody according to claim 1 wherein said antibody comprises an isolated antibody.

18. An antibody according to claim 1 wherein said fragment thereof comprises an antigen binding fragment thereof.

19. An antibody according to claim 1 and further comprising a label attached to said antibody or fragment thereof.

20. An antibody according to claim 19 wherein said label is selected from a group consisting of a radioactive element, magnetic particles, radioisotope, fluorescent dye, enzyme, toxin, signal, stain, and any combination thereof.

21. A method for detecting PAX8 in a biological sample comprising the steps of:
    contacting a biological sample with said antibody or fragment thereof according to claim 1; and
    detecting binding of said antibody with an antigen in said biological sample using said antibody detection element.

22. A method according to claim 21 wherein said biological sample is selected from a group consisting of a normal tissue, neoplastic tissue, kidney tissue, ovarian tissue, thyroid tissue, endometrial tissue, renal tissue, tonsil tissue, pancreas tissue, colon tissue, lymph node tissue, neoplastic pancreatic tissue, stomach tissue, bladder tissue, prostate tissue, lung tissue and breast tissue.

23. A method according to claim 21 wherein said detecting comprises a method selected from a group consisting of immunohistochemistry (IHC), IHC of FFPE, ICH of frozen-tissue sections, and ELISA.

* * * * *